(12) United States Patent
Asahara et al.

(10) Patent No.: US 8,409,563 B2
(45) Date of Patent: *Apr. 2, 2013

(54) PURINE-DERIVED SUBSTANCE-PRODUCING BACTERIUM AND A METHOD FOR PRODUCING A PURINE-DERIVED SUBSTANCE

(75) Inventors: Takayuki Asahara, Kawasaki (JP); Kiyoshi Matsuno, Kawasaki (JP); Yukiko Mori, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 1108 days.

This patent is subject to a terminal disclaimer.

(21) Appl. No.: 12/255,017

(22) Filed: Oct. 21, 2008

(65) Prior Publication Data

US 2009/0104665 A1    Apr. 23, 2009

Related U.S. Application Data

(63) Continuation of application No. PCT/JP2007/058356, filed on Apr. 17, 2007.

(30) Foreign Application Priority Data

Apr. 24, 2006 (JP) .................................. 2006-119315

(51) Int. Cl.
- C12P 19/40 (2006.01)
- A01N 63/00 (2006.01)
- A01N 65/00 (2009.01)

(52) U.S. Cl. ................. 424/93.462; 424/93.1; 424/93.2; 424/93.4; 424/93.46

(58) Field of Classification Search .................. None
See application file for complete search history.

(56) References Cited

U.S. PATENT DOCUMENTS

| | | | |
|---|---|---|---|
| 3,736,228 A | 5/1973 | Nakayama et al. | |
| 3,912,587 A | 10/1975 | Enei et al. | |
| 3,960,660 A | 6/1976 | Enei et al. | |
| 3,960,661 A | 6/1976 | Enei et al. | |
| 6,284,495 B1 | 9/2001 | Sato et al. | |
| 7,189,543 B2 | 3/2007 | Nishi et al. | |
| 7,211,416 B2 | 5/2007 | Asahara et al. | |
| 7,285,543 B2 | 10/2007 | Dang et al. | |
| 7,326,546 B2 * | 2/2008 | Matsuno et al. | 435/89 |
| 2004/0166575 A1 | 8/2004 | Tominaga et al. | |
| 2006/0014259 A9 | 1/2006 | Burke et al. | |
| 2006/0073559 A1 | 4/2006 | Ferrari et al. | |

FOREIGN PATENT DOCUMENTS

| | | |
|---|---|---|
| EP | 0 273 660 | 7/1988 |
| EP | 0 286 303 | 10/1988 |
| EP | 0 393 969 | 10/1990 |
| EP | 0 412 688 | 2/1991 |
| EP | 0 465 132 | 1/1992 |
| EP | 1 004 663 | 5/2000 |
| EP | 1225218 A1 * | 7/2002 |
| EP | 1 577 386 | 9/2005 |
| EP | 2 011 861 | 1/2009 |
| JP | 51-5075 | 2/1976 |
| JP | 54-17033 | 6/1979 |
| JP | 55-2956 | 1/1980 |
| JP | 55-45199 | 11/1980 |
| JP | 57-14160 | 3/1982 |
| JP | 57-41915 | 9/1982 |
| JP | 58-17592 | 4/1983 |
| JP | 58-158197 | 9/1983 |
| JP | 58-175493 | 10/1983 |
| JP | 59-028470 | 2/1984 |
| JP | 59-042895 | 3/1984 |
| JP | 60-156388 | 8/1985 |
| JP | 63-248394 | 10/1988 |
| JP | 64-027477 | 1/1989 |
| JP | 01-174385 | 7/1989 |
| JP | 03-58787 | 3/1991 |
| JP | 03-164185 | 7/1991 |
| JP | 05-084067 | 4/1993 |
| JP | 05-192164 | 8/1993 |
| JP | 2004-242610 | 9/2004 |
| WO | WO 99/03988 | 1/1999 |
| WO | WO03/083125 | 10/2003 |
| WO | WO2006/033668 | 3/2006 |

OTHER PUBLICATIONS

AEG96353 sequence alignment.*
Gu, X., et al., "Rv2131c gene product: An unconventional enzyme that is both inositol monophosphatase and fructose-1,6-biphosphatase," Biochem. Biophys. Res. Comm. 2006;339(3):897-904.
Supplementary Search Report for European Patent App. No. 07741792.1 (Sep. 3, 2009).
Final Notice of Preliminary Rejection for Korean Patent App. No. 10-2008-7028620 (Oct. 31, 2011) with English translation thereof.
Flores, S., et al., "Growth-Rate Recovery of *Escherichia coil* Cultures Carrying a Multicopy Plasmid by Engineering of the Pentose-Phosphate Pathway," Biotechnol. Bioeng. 2004;87(4):485-494.
Johansen, L. E., et al., "Definition of a Second *Bacillus subtilis* pur Regulon Comprising the *pur* and *xpt-pbuX* Operons plus *pbuG*, *nupG* (*yxjA*), and *pbuE* (*ydhL*)," J. Bacteriol. 2003;185(17):5200-5209.
Kamada, N., et al., "Significance of the non-oxidative route of the pentose phosphate pathway for supplying carbon to the ptirine-nucleotide pathway in *Corynebacterium ammoniagenes*," J. Ind. Microbial. 2003;30:129-132.
Kegg (Kyoto Encyclopedia of Genes and Genomes), Entry No. BG10942, *Bacillus subtilis*.
Kegg (Kyoto Encyclopedia of Genes and Genomes), Entry No. BG11739, *Bacillus subtilis*.
Kotani, Y., et al., "Inosine Accumulation by Mutants of *Brevibacterium ammoniagenes* Strain Improvement and Culture Conditions," Agric. Biol. Chem. 1978;42(2):399-405.

(Continued)

*Primary Examiner* — J. Hines
*Assistant Examiner* — Khaol Shahnan-Shah
(74) *Attorney, Agent, or Firm* — Shelly Guest Cermak; Cermak Nakajima LLP

(57) ABSTRACT

A purine-derived substance is produced by culturing a bacterium belonging to the genus *Bacillus* which is able to produce purine-derived substance and has been modified so that enzymatic activity of fructose bisphosphatase is decreased, and collecting the purine-derived substance from the medium or cells.

11 Claims, No Drawings

OTHER PUBLICATIONS

Saxild, H. H., et al., "Definition of the *Bacillus subtilis* PurR Operator Using Genetic and Bioinformatic Tools and Expansion of the PurR Regulon with *glyA, guaC, pbuG, xpt-pbuX, yqhZ-folD,* and *pbuO*," J. Bacteriol. 2001;183(21):6175-6183.

Lim, S-J, et al., "Amplification of the NADPH-Related Genes *zwf* and *gnd* for the Oddball Biosynthesis of PHB in an *E. coli* Transformant Harboring a Cloned phbCAB Operon," J. Biosci. Bioeng. 2002;93(6):543-549.

Tao, H., et al., "Engineering a Homo-Ethanol Pathway in *Escherichia coli*: Increased Glycolytic Flux and Levels of Expression of Glycolytic Genes during Xylose Fermentation," J. Bacteriol. 2001;183(10):2979-2988.

Weng, M., et al., "Identification of the *Bacillus subtilis* pur operon repressor," Proc. Natl. Acad. Sci. USA 1995;92:7455-7459.

International Preliminary Report on Patentability for PCT Patent App. No. PCT/JP2007/058356 (Nov. 27, 2008).

Fujita, Y., et al., "Isolation and Properties of a *Bacillus subtilis* Mutant Unable to Produce Fructose-Bisphosphate," J. Bacteriol. 1981;145(2):760-767.

International Search Report for PCT Patent App. No. PCT/JP2007/058356 (Jul. 17, 2007).

\* cited by examiner

SEQUENCE LISTING

<160> NUMBER OF SEQ ID NOS: 22

<210> SEQ ID NO 1
<211> LENGTH: 2013
<212> TYPE: DNA
<213> ORGANISM: Bacillus subtilis
<220> FEATURE:
<221> NAME/KEY: CDS
<222> LOCATION: (1)..(2013)

<400> SEQUENCE: 1

| | | | | | | | | | | | | | | | | |
|---|---|---|---|---|---|---|---|---|---|---|---|---|---|---|---|---|
| atg | ttt | aaa | aat | aat | gtc | ata | ctt | tta | aat | tca | cct | tat | cat | gca | cat | 48 |
| Met | Phe | Lys | Asn | Asn | Val | Ile | Leu | Leu | Asn | Ser | Pro | Tyr | His | Ala | His | |
| 1 | | | | 5 | | | | | 10 | | | | | 15 | | |
| gct | cat | aaa | gag | ggg | ttt | att | cta | aaa | agg | gga | tgg | acg | gtt | ttg | gaa | 96 |
| Ala | His | Lys | Glu | Gly | Phe | Ile | Leu | Lys | Arg | Gly | Trp | Thr | Val | Leu | Glu | |
| | | | 20 | | | | | 25 | | | | | 30 | | | |
| agc | aag | tac | cta | gat | cta | ctc | gca | caa | aaa | tac | gat | tgt | gaa | gaa | aaa | 144 |
| Ser | Lys | Tyr | Leu | Asp | Leu | Leu | Ala | Gln | Lys | Tyr | Asp | Cys | Glu | Glu | Lys | |
| | | 35 | | | | | 40 | | | | | 45 | | | | |
| gtg | gta | aca | gaa | atc | atc | aat | ttg | aaa | gcg | ata | ttg | aac | ctg | cca | aaa | 192 |
| Val | Val | Thr | Glu | Ile | Ile | Asn | Leu | Lys | Ala | Ile | Leu | Asn | Leu | Pro | Lys | |
| 50 | | | | | 55 | | | | | 60 | | | | | | |
| ggc | acc | gag | cat | ttt | gtc | agt | gat | ctg | cac | gga | gag | tat | cag | gca | ttc | 240 |
| Gly | Thr | Glu | His | Phe | Val | Ser | Asp | Leu | His | Gly | Glu | Tyr | Gln | Ala | Phe | |
| 65 | | | | 70 | | | | | 75 | | | | | 80 | | |
| cag | cac | gtg | ttg | cgc | aat | ggt | tca | gga | cga | gtc | aaa | gag | aag | ata | cgc | 288 |
| Gln | His | Val | Leu | Arg | Asn | Gly | Ser | Gly | Arg | Val | Lys | Glu | Lys | Ile | Arg | |
| | | | 85 | | | | | 90 | | | | | 95 | | | |
| gac | atc | ttc | agc | ggt | gtc | att | tac | gat | aga | gaa | att | gat | gaa | tta | gca | 336 |
| Asp | Ile | Phe | Ser | Gly | Val | Ile | Tyr | Asp | Arg | Glu | Ile | Asp | Glu | Leu | Ala | |
| | | | | 100 | | | | | 105 | | | | | 110 | | |
| gca | ttg | gtc | tat | tat | ccg | gaa | gac | aaa | ctg | aaa | tta | atc | aaa | cat | gac | 384 |
| Ala | Leu | Val | Tyr | Tyr | Pro | Glu | Asp | Lys | Leu | Lys | Leu | Ile | Lys | His | Asp | |
| | | | 115 | | | | | 120 | | | | | 125 | | | |
| ttt | gat | gcg | aaa | gaa | gcg | tta | aac | gag | tgg | tat | aaa | gaa | acg | att | cat | 432 |
| Phe | Asp | Ala | Lys | Glu | Ala | Leu | Asn | Glu | Trp | Tyr | Lys | Glu | Thr | Ile | His | |
| | 130 | | | | | 135 | | | | | 140 | | | | | |
| cga | atg | att | aag | ctc | gtt | tca | tat | tgc | tcc | tct | aag | tat | acc | cgc | tcc | 480 |
| Arg | Met | Ile | Lys | Leu | Val | Ser | Tyr | Cys | Ser | Ser | Lys | Tyr | Thr | Arg | Ser | |
| 145 | | | | | 150 | | | | | 155 | | | | | 160 | |
| aaa | tta | cgc | aaa | gca | ctg | cct | gcc | caa | ttt | gct | tat | att | acg | gag | gag | 528 |
| Lys | Leu | Arg | Lys | Ala | Leu | Pro | Ala | Gln | Phe | Ala | Tyr | Ile | Thr | Glu | Glu | |
| | | | | 165 | | | | | 170 | | | | | 175 | | |
| ctg | tta | tac | aaa | aca | gaa | caa | gct | ggc | aac | aag | gag | caa | tat | tac | tcc | 576 |
| Leu | Leu | Tyr | Lys | Thr | Glu | Gln | Ala | Gly | Asn | Lys | Glu | Gln | Tyr | Tyr | Ser | |
| | | | 180 | | | | | 185 | | | | | 190 | | | |
| gaa | atc | att | gat | cag | atc | att | gaa | ctt | ggc | caa | gcc | gat | aag | ctg | atc | 624 |
| Glu | Ile | Ile | Asp | Gln | Ile | Ile | Glu | Leu | Gly | Gln | Ala | Asp | Lys | Leu | Ile | |
| | | | 195 | | | | | 200 | | | | | 205 | | | |
| acc | ggc | ctt | gct | tac | agc | gtt | cag | cga | ttg | gtg | gtc | gac | cat | ctg | cat | 672 |
| Thr | Gly | Leu | Ala | Tyr | Ser | Val | Gln | Arg | Leu | Val | Val | Asp | His | Leu | His | |
| | | 210 | | | | | 215 | | | | | 220 | | | | |
| gtg | gtc | ggc | gat | att | tat | gac | cgc | ggc | ccg | cag | ccg | gat | aga | att | atg | 720 |
| Val | Val | Gly | Asp | Ile | Tyr | Asp | Arg | Gly | Pro | Gln | Pro | Asp | Arg | Ile | Met | |
| 225 | | | | | 230 | | | | | 235 | | | | | 240 | |
| gaa | gaa | ctg | atc | aac | tat | cat | tct | gtc | gat | att | cag | tgg | gga | aat | cac | 768 |
| Glu | Glu | Leu | Ile | Asn | Tyr | His | Ser | Val | Asp | Ile | Gln | Trp | Gly | Asn | His | |
| | | | | 245 | | | | | 250 | | | | | 255 | | |
| gat | gtc | ctt | tgg | atc | ggc | gcc | tat | tcc | ggt | tcc | aaa | gtg | tgc | ctg | gcc | 816 |

```
                Asp Val Leu Trp Ile Gly Ala Tyr Ser Gly Ser Lys Val Cys Leu Ala
                            260                 265                 270 aat att atc cgc atc tgt gcc cgc tac gac aac ctg gat att att gag        864
Asn Ile Ile Arg Ile Cys Ala Arg Tyr Asp Asn Leu Asp Ile Ile Glu
                275                 280                 285 gac gtg tac ggc atc aac ctg aga ccg ctg ctg aac ctg gcc gaa aaa        912
Asp Val Tyr Gly Ile Asn Leu Arg Pro Leu Leu Asn Leu Ala Glu Lys
            290                 295                 300 tat tat gat gat aat cca gcg ttc cgt cca aaa gca gac gaa aac agg        960
Tyr Tyr Asp Asp Asn Pro Ala Phe Arg Pro Lys Ala Asp Glu Asn Arg
305                 310                 315                 320 cca gag gat gag att aag caa atc aca aaa atc cat caa gcg att gcc       1008
Pro Glu Asp Glu Ile Lys Gln Ile Thr Lys Ile His Gln Ala Ile Ala
                325                 330                 335 atg atc caa ttc aag ctt gag agc ccg att atc aag aga cgg ccg aac       1056
Met Ile Gln Phe Lys Leu Glu Ser Pro Ile Ile Lys Arg Arg Pro Asn
                340                 345                 350 ttt aat atg gaa gag cgg ctg tta tta gag aaa ata gac tat gac aaa       1104
Phe Asn Met Glu Glu Arg Leu Leu Leu Glu Lys Ile Asp Tyr Asp Lys
                355                 360                 365 aat gaa atc acg ctg aac gga aaa aca tat caa ctg gaa aac acc tgc       1152
Asn Glu Ile Thr Leu Asn Gly Lys Thr Tyr Gln Leu Glu Asn Thr Cys
370                 375                 380 ttt gcg acg att aat ccg gag cag cca gat cag cta tta gaa gaa gaa       1200
Phe Ala Thr Ile Asn Pro Glu Gln Pro Asp Gln Leu Leu Glu Glu Glu
385                 390                 395                 400 gca gaa gtc ata gac aag ctg cta ttc tct gtc cag cat tcc gaa aag       1248
Ala Glu Val Ile Asp Lys Leu Leu Phe Ser Val Gln His Ser Glu Lys
                405                 410                 415 ctg ggc cgc cat atg aat ttt atg atg aaa aaa ggc agc ctt tat tta       1296
Leu Gly Arg His Met Asn Phe Met Met Lys Lys Gly Ser Leu Tyr Leu
                420                 425                 430 aaa tat aac ggc aac ctg ttg att cac ggc tgt att cca gtt gat gaa       1344
Lys Tyr Asn Gly Asn Leu Leu Ile His Gly Cys Ile Pro Val Asp Glu
            435                 440                 445 aac ggc aat atg gaa acg atg atg att gag gat aaa ccg tat gcg ggc       1392
Asn Gly Asn Met Glu Thr Met Met Ile Glu Asp Lys Pro Tyr Ala Gly
            450                 455                 460 cgt gag ctg ctc gat gta ttt gaa cga ttc ttg cgg gaa gcc ttt gcc       1440
Arg Glu Leu Leu Asp Val Phe Glu Arg Phe Leu Arg Glu Ala Phe Ala
465                 470                 475                 480 cac ccg gaa gaa acc gat gac ctg gcg aca gat atg gct tgg tat tta       1488
His Pro Glu Glu Thr Asp Asp Leu Ala Thr Asp Met Ala Trp Tyr Leu
                485                 490                 495 tgg aca ggc gaa tac tcc tcc ctc ttc gga aaa cgc gcc atg acg aca       1536
Trp Thr Gly Glu Tyr Ser Ser Leu Phe Gly Lys Arg Ala Met Thr Thr
                500                 505                 510 ttt gag cgc tat ttc atc aaa gag aag gaa acg cat aaa gag aag aaa       1584
Phe Glu Arg Tyr Phe Ile Lys Glu Lys Glu Thr His Lys Glu Lys Lys
                515                 520                 525 aac ccg tat tat tat tta cga gaa gac gag gca acc tgc cga aac atc       1632
Asn Pro Tyr Tyr Tyr Leu Arg Glu Asp Glu Ala Thr Cys Arg Asn Ile
            530                 535                 540 ctg gca gaa ttc ggc ctc aat cca gat cac ggc cat atc atc aac ggc       1680
Leu Ala Glu Phe Gly Leu Asn Pro Asp His Gly His Ile Ile Asn Gly
545                 550                 555                 560 cat aca cct gta aaa gaa atc gaa gga gaa gac cca atc aaa gca aac       1728
His Thr Pro Val Lys Glu Ile Glu Gly Glu Asp Pro Ile Lys Ala Asn
                565                 570                 575 gga aaa atg atc gtc atc gac ggc ggc ttc tcc aaa gcc tac caa tcc       1776
```

```
                                          -continued

Gly Lys Met Ile Val Ile Asp Gly Gly Phe Ser Lys Ala Tyr Gln Ser
        580                 585                 590 aca aca ggc atc gcc ggc tac acg ctg cta tac aac tcc tac ggc atg    1824
Thr Thr Gly Ile Ala Gly Tyr Thr Leu Leu Tyr Asn Ser Tyr Gly Met
        595                 600                 605 cag ctc gtc gcc cat aaa cac ttc aat tcc aag gca gaa gtc cta agc    1872
Gln Leu Val Ala His Lys His Phe Asn Ser Lys Ala Glu Val Leu Ser
610                 615                 620 acc gga acc gac gtc tta acg gtc aaa cga tta gtg gac aaa gag ctt    1920
Thr Gly Thr Asp Val Leu Thr Val Lys Arg Leu Val Asp Lys Glu Leu
625                 630                 635                 640 gag cgg aag aaa gtg aag gaa acg aat gtg ggt gag gaa ttg ttg cag    1968
Glu Arg Lys Lys Val Lys Glu Thr Asn Val Gly Glu Glu Leu Leu Gln
                645                 650                 655 gaa gtt gcg att tta gag agt ttg cgg gag tat cgg tat atg aag        2013
Glu Val Ala Ile Leu Glu Ser Leu Arg Glu Tyr Arg Tyr Met Lys
            660                 665                 670

<210> SEQ ID NO 2
<211> LENGTH: 671
<212> TYPE: PRT
<213> ORGANISM: Bacillus subtilis

<400> SEQUENCE: 2

Met Phe Lys Asn Asn Val Ile Leu Leu Asn Ser Pro Tyr His Ala His
1               5                   10                  15

Ala His Lys Glu Gly Phe Ile Leu Lys Arg Gly Trp Thr Val Leu Glu
            20                  25                  30

Ser Lys Tyr Leu Asp Leu Leu Ala Gln Lys Tyr Asp Cys Glu Glu Lys
        35                  40                  45

Val Val Thr Glu Ile Ile Asn Leu Lys Ala Ile Leu Asn Leu Pro Lys
    50                  55                  60

Gly Thr Glu His Phe Val Ser Asp Leu His Gly Glu Tyr Gln Ala Phe
65                  70                  75                  80

Gln His Val Leu Arg Asn Gly Ser Gly Arg Val Lys Glu Lys Ile Arg
                85                  90                  95

Asp Ile Phe Ser Gly Val Ile Tyr Asp Arg Glu Ile Asp Glu Leu Ala
            100                 105                 110

Ala Leu Val Tyr Tyr Pro Glu Asp Lys Leu Lys Leu Ile Lys His Asp
        115                 120                 125

Phe Asp Ala Lys Glu Ala Leu Asn Glu Trp Tyr Lys Glu Thr Ile His
    130                 135                 140

Arg Met Ile Lys Leu Val Ser Tyr Cys Ser Ser Lys Tyr Thr Arg Ser
145                 150                 155                 160

Lys Leu Arg Lys Ala Leu Pro Ala Gln Phe Ala Tyr Ile Thr Glu Glu
                165                 170                 175

Leu Leu Tyr Lys Thr Glu Gln Ala Gly Asn Lys Glu Gln Tyr Tyr Ser
            180                 185                 190

Glu Ile Ile Asp Gln Ile Ile Glu Leu Gly Gln Ala Asp Lys Leu Ile
        195                 200                 205

Thr Gly Leu Ala Tyr Ser Val Gln Arg Leu Val Val Asp His Leu His
    210                 215                 220

Val Val Gly Asp Ile Tyr Asp Arg Gly Pro Gln Pro Arg Ile Met
225                 230                 235                 240

Glu Glu Leu Ile Asn Tyr His Ser Val Asp Ile Gln Trp Gly Asn His
                245                 250                 255

Asp Val Leu Trp Ile Gly Ala Tyr Ser Gly Ser Lys Val Cys Leu Ala
```

```
            260                 265                 270
Asn Ile Ile Arg Ile Cys Ala Arg Tyr Asp Asn Leu Asp Ile Ile Glu
        275                 280                 285
Asp Val Tyr Gly Ile Asn Leu Arg Pro Leu Leu Asn Leu Ala Glu Lys
290                 295                 300
Tyr Tyr Asp Asp Asn Pro Ala Phe Arg Pro Lys Ala Asp Glu Asn Arg
305                 310                 315                 320
Pro Glu Asp Glu Ile Lys Gln Ile Thr Lys Ile His Gln Ala Ile Ala
                325                 330                 335
Met Ile Gln Phe Lys Leu Glu Ser Pro Ile Ile Lys Arg Arg Pro Asn
            340                 345                 350
Phe Asn Met Glu Glu Arg Leu Leu Leu Glu Lys Ile Asp Tyr Asp Lys
        355                 360                 365
Asn Glu Ile Thr Leu Asn Gly Lys Thr Tyr Gln Leu Glu Asn Thr Cys
    370                 375                 380
Phe Ala Thr Ile Asn Pro Glu Gln Pro Asp Gln Leu Leu Glu Glu Glu
385                 390                 395                 400
Ala Glu Val Ile Asp Lys Leu Leu Phe Ser Val Gln His Ser Glu Lys
                405                 410                 415
Leu Gly Arg His Met Asn Phe Met Met Lys Lys Gly Ser Leu Tyr Leu
            420                 425                 430
Lys Tyr Asn Gly Asn Leu Leu Ile His Gly Cys Ile Pro Val Asp Glu
        435                 440                 445
Asn Gly Asn Met Glu Thr Met Met Ile Glu Asp Lys Pro Tyr Ala Gly
    450                 455                 460
Arg Glu Leu Leu Asp Val Phe Glu Arg Phe Leu Arg Glu Ala Phe Ala
465                 470                 475                 480
His Pro Glu Glu Thr Asp Asp Leu Ala Thr Asp Met Ala Trp Tyr Leu
                485                 490                 495
Trp Thr Gly Glu Tyr Ser Ser Leu Phe Gly Lys Arg Ala Met Thr Thr
            500                 505                 510
Phe Glu Arg Tyr Phe Ile Lys Glu Lys Glu Thr His Lys Glu Lys Lys
        515                 520                 525
Asn Pro Tyr Tyr Tyr Leu Arg Glu Asp Glu Ala Thr Cys Arg Asn Ile
    530                 535                 540
Leu Ala Glu Phe Gly Leu Asn Pro Asp His Gly His Ile Ile Asn Gly
545                 550                 555                 560
His Thr Pro Val Lys Glu Ile Glu Gly Glu Asp Pro Ile Lys Ala Asn
                565                 570                 575
Gly Lys Met Ile Val Ile Asp Gly Gly Phe Ser Lys Ala Tyr Gln Ser
            580                 585                 590
Thr Thr Gly Ile Ala Gly Tyr Thr Leu Leu Tyr Asn Ser Tyr Gly Met
        595                 600                 605
Gln Leu Val Ala His Lys His Phe Asn Ser Lys Ala Glu Val Leu Ser
    610                 615                 620
Thr Gly Thr Asp Val Leu Thr Val Lys Arg Leu Val Asp Lys Glu Leu
625                 630                 635                 640
Glu Arg Lys Lys Val Lys Glu Thr Asn Val Gly Glu Leu Leu Gln
                645                 650                 655
Glu Val Ala Ile Leu Glu Ser Leu Arg Glu Tyr Arg Tyr Met Lys
            660                 665                 670

<210> SEQ ID NO 3
<211> LENGTH: 954
```

```
<212> TYPE: DNA
<213> ORGANISM: Bacillus subtilis
<220> FEATURE:
<221> NAME/KEY: CDS
<222> LOCATION: (1)..(954)

<400> SEQUENCE: 3 atg tct aat caa tac gga gat aag aat tta aag att ttt tct ttg aat        48
Met Ser Asn Gln Tyr Gly Asp Lys Asn Leu Lys Ile Phe Ser Leu Asn
1               5                  10                  15 tcg aat cca gag ctt gca aaa gaa atc gca gat ata gtt gga gtt caa        96
Ser Asn Pro Glu Leu Ala Lys Glu Ile Ala Asp Ile Val Gly Val Gln
            20                  25                  30 tta ggg aaa tgt tct gtc aca aga ttt agt gac ggg gaa gtc caa att       144
Leu Gly Lys Cys Ser Val Thr Arg Phe Ser Asp Gly Glu Val Gln Ile
        35                  40                  45 aat atc gaa gaa agt att cgc gga tgt gat tgt tac atc atc cag tct       192
Asn Ile Glu Glu Ser Ile Arg Gly Cys Asp Cys Tyr Ile Ile Gln Ser
    50                  55                  60 aca agt gac ccc gtt aac gag cat att atg gaa ctg ctg att atg gta       240
Thr Ser Asp Pro Val Asn Glu His Ile Met Glu Leu Leu Ile Met Val
65                  70                  75                  80 gat gcg tta aaa cgc gct tct gca aaa acg att aac att gtt att cct       288
Asp Ala Leu Lys Arg Ala Ser Ala Lys Thr Ile Asn Ile Val Ile Pro
                85                  90                  95 tat tac ggt tat gcg cgt caa gac aga aaa gca aga tcc cgt gag cca       336
Tyr Tyr Gly Tyr Ala Arg Gln Asp Arg Lys Ala Arg Ser Arg Glu Pro
            100                 105                 110 atc aca gct aaa ctt ttc gct aac ctg ctt gaa aca gcc ggt gcg act       384
Ile Thr Ala Lys Leu Phe Ala Asn Leu Leu Glu Thr Ala Gly Ala Thr
        115                 120                 125 cgt gtg att gca ctt gac ctg cat gcg ccg caa att caa gga ttc ttt       432
Arg Val Ile Ala Leu Asp Leu His Ala Pro Gln Ile Gln Gly Phe Phe
    130                 135                 140 gat ata ccg att gac cac tta atg ggt gtt ccg att tta gga gaa tat       480
Asp Ile Pro Ile Asp His Leu Met Gly Val Pro Ile Leu Gly Glu Tyr
145                 150                 155                 160 ttt gaa ggc aaa aat ctt gaa gat atc gtc att gtt tca cca gac cat       528
Phe Glu Gly Lys Asn Leu Glu Asp Ile Val Ile Val Ser Pro Asp His
                165                 170                 175 ggc ggt gtg aca cgt gcc cgc aaa ctg gct gac cga cta aaa gcg cca       576
Gly Gly Val Thr Arg Ala Arg Lys Leu Ala Asp Arg Leu Lys Ala Pro
            180                 185                 190 att gcg att atc gat aaa cgc cgt ccg cgt cca aac gtg gcg gaa gtc       624
Ile Ala Ile Ile Asp Lys Arg Arg Pro Arg Pro Asn Val Ala Glu Val
        195                 200                 205 atg aat att gta ggt aac atc gaa ggg aag act gct atc ctc atc gat       672
Met Asn Ile Val Gly Asn Ile Glu Gly Lys Thr Ala Ile Leu Ile Asp
    210                 215                 220 gac att att gat act gca ggt acg att aca ctt gct gct aat gcg ctc       720
Asp Ile Ile Asp Thr Ala Gly Thr Ile Thr Leu Ala Ala Asn Ala Leu
225                 230                 235                 240 gtt gaa aac gga gcg aaa gaa gta tat gca tgc tgt aca cac cct gta       768
Val Glu Asn Gly Ala Lys Glu Val Tyr Ala Cys Cys Thr His Pro Val
                245                 250                 255 cta tca ggc cct gcg gtt gaa cgg att aat aat tca aca att aaa gag       816
Leu Ser Gly Pro Ala Val Glu Arg Ile Asn Asn Ser Thr Ile Lys Glu
            260                 265                 270 ctt gtt gtg aca aac agc atc aag ctt cct gaa gaa aag aaa att gaa       864
Leu Val Val Thr Asn Ser Ile Lys Leu Pro Glu Glu Lys Lys Ile Glu
        275                 280                 285
```

```
cgc ttt aag cag ctt tca gtc gga ccg ctt ctg gcc gaa gcg att att    912
Arg Phe Lys Gln Leu Ser Val Gly Pro Leu Leu Ala Glu Ala Ile Ile
    290                 295                 300 cgc gtt cat gag cag caa tca gtc agc tat ctg ttc agc taa            954
Arg Val His Glu Gln Gln Ser Val Ser Tyr Leu Phe Ser
305                 310                 315
```

<210> SEQ ID NO 4
<211> LENGTH: 317
<212> TYPE: PRT
<213> ORGANISM: Bacillus subtilis

<400> SEQUENCE: 4

```
Met Ser Asn Gln Tyr Gly Asp Lys Asn Leu Lys Ile Phe Ser Leu Asn
1               5                   10                  15

Ser Asn Pro Glu Leu Ala Lys Glu Ile Ala Asp Ile Val Gly Val Gln
            20                  25                  30

Leu Gly Lys Cys Ser Val Thr Arg Phe Ser Asp Gly Glu Val Gln Ile
        35                  40                  45

Asn Ile Glu Glu Ser Ile Arg Gly Cys Asp Cys Tyr Ile Ile Gln Ser
    50                  55                  60

Thr Ser Asp Pro Val Asn Glu His Ile Met Glu Leu Leu Ile Met Val
65                  70                  75                  80

Asp Ala Leu Lys Arg Ala Ser Ala Lys Thr Ile Asn Ile Val Ile Pro
                85                  90                  95

Tyr Tyr Gly Tyr Ala Arg Gln Asp Arg Lys Ala Arg Ser Arg Glu Pro
            100                 105                 110

Ile Thr Ala Lys Leu Phe Ala Asn Leu Leu Glu Thr Ala Gly Ala Thr
        115                 120                 125

Arg Val Ile Ala Leu Asp Leu His Ala Pro Gln Ile Gln Gly Phe Phe
    130                 135                 140

Asp Ile Pro Ile Asp His Leu Met Gly Val Pro Ile Leu Gly Glu Tyr
145                 150                 155                 160

Phe Glu Gly Lys Asn Leu Glu Asp Ile Val Val Ser Pro Asp His
                165                 170                 175

Gly Gly Val Thr Arg Ala Arg Lys Leu Ala Asp Arg Leu Lys Ala Pro
            180                 185                 190

Ile Ala Ile Ile Asp Lys Arg Arg Pro Arg Pro Asn Val Ala Glu Val
        195                 200                 205

Met Asn Ile Val Gly Asn Ile Glu Gly Lys Thr Ala Ile Leu Ile Asp
    210                 215                 220

Asp Ile Ile Asp Thr Ala Gly Thr Ile Thr Leu Ala Ala Asn Ala Leu
225                 230                 235                 240

Val Glu Asn Gly Ala Lys Glu Val Tyr Ala Cys Cys Thr His Pro Val
                245                 250                 255

Leu Ser Gly Pro Ala Val Glu Arg Ile Asn Asn Ser Thr Ile Lys Glu
            260                 265                 270

Leu Val Val Thr Asn Ser Ile Lys Leu Pro Glu Glu Lys Lys Ile Glu
        275                 280                 285

Arg Phe Lys Gln Leu Ser Val Gly Pro Leu Leu Ala Glu Ala Ile Ile
    290                 295                 300

Arg Val His Glu Gln Gln Ser Val Ser Tyr Leu Phe Ser
305                 310                 315
```

<210> SEQ ID NO 5
<211> LENGTH: 858
<212> TYPE: DNA

```
<213> ORGANISM: Bacillus subtilis
<220> FEATURE:
<221> NAME/KEY: CDS
<222> LOCATION: (1)..(858)

<400> SEQUENCE: 5 atg aag ttt cgt cgc agc ggc aga ttg gtg gac tta aca aat tat ttg      48
Met Lys Phe Arg Arg Ser Gly Arg Leu Val Asp Leu Thr Asn Tyr Leu
1               5                   10                  15 tta acc cat ccg cac gag tta ata ccg cta acc ttt ttc tct gag cgg      96
Leu Thr His Pro His Glu Leu Ile Pro Leu Thr Phe Phe Ser Glu Arg
            20                  25                  30 tat gaa tct gca aaa tca tcg atc agt gaa gat tta aca att att aaa     144
Tyr Glu Ser Ala Lys Ser Ser Ile Ser Glu Asp Leu Thr Ile Ile Lys
        35                  40                  45 caa acc ttt gaa cag cag ggg att ggt act ttg ctt act gtt ccc gga     192
Gln Thr Phe Glu Gln Gln Gly Ile Gly Thr Leu Leu Thr Val Pro Gly
    50                  55                  60 gct gcc gga ggc gtt aaa tat att ccg aaa atg aag cag gct gaa gct     240
Ala Ala Gly Gly Val Lys Tyr Ile Pro Lys Met Lys Gln Ala Glu Ala
65                  70                  75                  80 gaa gag ttt gtg cag aca ctt gga cag tcg ctg gca aat cct gag cgt     288
Glu Glu Phe Val Gln Thr Leu Gly Gln Ser Leu Ala Asn Pro Glu Arg
                85                  90                  95 atc ctt ccg ggc ggt tat gta tat tta acg gat atc tta gga aag cca     336
Ile Leu Pro Gly Gly Tyr Val Tyr Leu Thr Asp Ile Leu Gly Lys Pro
            100                 105                 110 tct gta ctc tcc aag gta ggg aag ctg ttt gct tcc gtg ttt gca gag     384
Ser Val Leu Ser Lys Val Gly Lys Leu Phe Ala Ser Val Phe Ala Glu
        115                 120                 125 cgc gaa att gat gtt gtc atg acc gtt gcc acg aaa ggc atc cct ctt     432
Arg Glu Ile Asp Val Val Met Thr Val Ala Thr Lys Gly Ile Pro Leu
    130                 135                 140 gcg tac gca gct gca agc tat ttg aat gtg cct gtt gtg atc gtt cgt     480
Ala Tyr Ala Ala Ala Ser Tyr Leu Asn Val Pro Val Val Ile Val Arg
145                 150                 155                 160 aaa gac aat aag gta aca gag ggc tcc aca gtc agc att aat tac gtt     528
Lys Asp Asn Lys Val Thr Glu Gly Ser Thr Val Ser Ile Asn Tyr Val
                165                 170                 175 tca ggc tcc tca aac cgc att caa aca atg tca ctt gcg aaa aga agc     576
Ser Gly Ser Ser Asn Arg Ile Gln Thr Met Ser Leu Ala Lys Arg Ser
            180                 185                 190 atg aaa acg ggt tca aac gta ctc att att gat gac ttt atg aaa gca     624
Met Lys Thr Gly Ser Asn Val Leu Ile Ile Asp Asp Phe Met Lys Ala
        195                 200                 205 ggc ggc acc att aat ggt atg att aac ctg ttg gat gag ttt aac gca     672
Gly Gly Thr Ile Asn Gly Met Ile Asn Leu Leu Asp Glu Phe Asn Ala
    210                 215                 220 aat gtg gcg gga atc ggc gtc tta gtt gaa gcc gaa gga gta gat gaa     720
Asn Val Ala Gly Ile Gly Val Leu Val Glu Ala Glu Gly Val Asp Glu
225                 230                 235                 240 cgt ctt gtt gac gaa tat atg tca ctt ctt act ctt tca acc atc aac     768
Arg Leu Val Asp Glu Tyr Met Ser Leu Leu Thr Leu Ser Thr Ile Asn
                245                 250                 255 atg aaa gag aag tcc att gaa att cag aat ggc aat ttt ctg cgt ttt     816
Met Lys Glu Lys Ser Ile Glu Ile Gln Asn Gly Asn Phe Leu Arg Phe
            260                 265                 270 ttt aaa gac aat ctt tta aag aat gga gag aca gaa tca tga             858
Phe Lys Asp Asn Leu Leu Lys Asn Gly Glu Thr Glu Ser
        275                 280                 285
```

<210> SEQ ID NO 6
<211> LENGTH: 285
<212> TYPE: PRT
<213> ORGANISM: Bacillus subtilis

<400> SEQUENCE: 6

Met Lys Phe Arg Arg Ser Gly Arg Leu Val Asp Leu Thr Asn Tyr Leu
1               5                   10                  15

Leu Thr His Pro His Glu Leu Ile Pro Leu Thr Phe Phe Ser Glu Arg
            20                  25                  30

Tyr Glu Ser Ala Lys Ser Ser Ile Ser Glu Asp Leu Thr Ile Ile Lys
        35                  40                  45

Gln Thr Phe Glu Gln Gln Gly Ile Gly Thr Leu Leu Thr Val Pro Gly
    50                  55                  60

Ala Ala Gly Gly Val Lys Tyr Ile Pro Lys Met Lys Gln Ala Glu Ala
65                  70                  75                  80

Glu Glu Phe Val Gln Thr Leu Gly Gln Ser Leu Ala Asn Pro Glu Arg
                85                  90                  95

Ile Leu Pro Gly Gly Tyr Val Tyr Leu Thr Asp Ile Leu Gly Lys Pro
            100                 105                 110

Ser Val Leu Ser Lys Val Gly Lys Leu Phe Ala Ser Val Phe Ala Glu
        115                 120                 125

Arg Glu Ile Asp Val Val Met Thr Val Ala Thr Lys Gly Ile Pro Leu
    130                 135                 140

Ala Tyr Ala Ala Ala Ser Tyr Leu Asn Val Pro Val Val Ile Val Arg
145                 150                 155                 160

Lys Asp Asn Lys Val Thr Glu Gly Ser Thr Val Ser Ile Asn Tyr Val
                165                 170                 175

Ser Gly Ser Ser Asn Arg Ile Gln Thr Met Ser Leu Ala Lys Arg Ser
            180                 185                 190

Met Lys Thr Gly Ser Asn Val Leu Ile Ile Asp Asp Phe Met Lys Ala
        195                 200                 205

Gly Gly Thr Ile Asn Gly Met Ile Asn Leu Leu Asp Glu Phe Asn Ala
    210                 215                 220

Asn Val Ala Gly Ile Gly Val Leu Val Glu Ala Gly Val Asp Glu
225                 230                 235                 240

Arg Leu Val Asp Glu Tyr Met Ser Leu Leu Thr Leu Ser Thr Ile Asn
                245                 250                 255

Met Lys Glu Lys Ser Ile Glu Ile Gln Asn Gly Asn Phe Leu Arg Phe
            260                 265                 270

Phe Lys Asp Asn Leu Leu Lys Asn Gly Glu Thr Glu Ser
        275                 280                 285

<210> SEQ ID NO 7
<211> LENGTH: 702
<212> TYPE: DNA
<213> ORGANISM: Bacillus subtilis
<220> FEATURE:
<221> NAME/KEY: CDS
<222> LOCATION: (1)..(702)

<400> SEQUENCE: 7 atg agt gta cat ata ggt gct gaa aaa gga caa att gcg gat act gtg     48
Met Ser Val His Ile Gly Ala Glu Lys Gly Gln Ile Ala Asp Thr Val
1               5                   10                  15 ctt ttg ccg gga gat cct ctc aga gca aaa ttt att gca gaa acg tat     96
Leu Leu Pro Gly Asp Pro Leu Arg Ala Lys Phe Ile Ala Glu Thr Tyr
            20                  25                  30

```
ctt gaa aat gta gaa tgc tac aat gaa gtc aga ggc atg tat gga ttt      144
Leu Glu Asn Val Glu Cys Tyr Asn Glu Val Arg Gly Met Tyr Gly Phe
         35                  40                  45 acg ggt aca tat aaa ggt aaa aaa atc tca gta caa ggc acg gga atg      192
Thr Gly Thr Tyr Lys Gly Lys Lys Ile Ser Val Gln Gly Thr Gly Met
 50                  55                  60 gga gtt ccg tct att tca att tat gtg aat gaa tta att caa agc tac      240
Gly Val Pro Ser Ile Ser Ile Tyr Val Asn Glu Leu Ile Gln Ser Tyr
 65                  70                  75                  80 gat gtg caa aat cta ata aga gtc ggt tcc tgc ggc gct att cgt aaa      288
Asp Val Gln Asn Leu Ile Arg Val Gly Ser Cys Gly Ala Ile Arg Lys
                 85                  90                  95 gat gtc aaa gtg cga gac gtc att ttg gcg atg acc tcc act gat           336
Asp Val Lys Val Arg Asp Val Ile Leu Ala Met Thr Ser Thr Asp
                100                 105                 110 tca caa atg aac aga gtt gct ttc gga agc gtt gat ttt gcg cct tgc      384
Ser Gln Met Asn Arg Val Ala Phe Gly Ser Val Asp Phe Ala Pro Cys
            115                 120                 125 gca gat ttc gag ctt tta aaa aat gcc tat gat gcc gca aag gat aaa      432
Ala Asp Phe Glu Leu Leu Lys Asn Ala Tyr Asp Ala Ala Lys Asp Lys
130                 135                 140 ggt gtg ccg gtg act gta gga agc gta ttt aca gct gac cag ttc tac      480
Gly Val Pro Val Thr Val Gly Ser Val Phe Thr Ala Asp Gln Phe Tyr
145                 150                 155                 160 aat gac gat tcg caa att gaa aaa ctt gca aaa tac ggt gtg ctt ggc      528
Asn Asp Asp Ser Gln Ile Glu Lys Leu Ala Lys Tyr Gly Val Leu Gly
                165                 170                 175 gtt gaa atg gaa aca act gca ttg tat aca tta gca gcg aag cac gga      576
Val Glu Met Glu Thr Thr Ala Leu Tyr Thr Leu Ala Ala Lys His Gly
            180                 185                 190 aga aaa gcc ctg tca att ctc acc gtg agt gat cac gta tta aca gga      624
Arg Lys Ala Leu Ser Ile Leu Thr Val Ser Asp His Val Leu Thr Gly
        195                 200                 205 gaa gaa acg aca gcg gaa gag cgt caa acg aca ttt cat gat atg ata      672
Glu Glu Thr Thr Ala Glu Glu Arg Gln Thr Thr Phe His Asp Met Ile
    210                 215                 220 gaa gtg gct tta cat tcc gta tca caa taa                              702
Glu Val Ala Leu His Ser Val Ser Gln
225                 230
```

<210> SEQ ID NO 8
<211> LENGTH: 233
<212> TYPE: PRT
<213> ORGANISM: Bacillus subtilis

<400> SEQUENCE: 8

```
Met Ser Val His Ile Gly Ala Glu Lys Gly Gln Ile Ala Asp Thr Val
 1               5                  10                  15

Leu Leu Pro Gly Asp Pro Leu Arg Ala Lys Phe Ile Ala Glu Thr Tyr
                20                  25                  30

Leu Glu Asn Val Glu Cys Tyr Asn Glu Val Arg Gly Met Tyr Gly Phe
            35                  40                  45

Thr Gly Thr Tyr Lys Gly Lys Lys Ile Ser Val Gln Gly Thr Gly Met
 50                  55                  60

Gly Val Pro Ser Ile Ser Ile Tyr Val Asn Glu Leu Ile Gln Ser Tyr
 65                  70                  75                  80

Asp Val Gln Asn Leu Ile Arg Val Gly Ser Cys Gly Ala Ile Arg Lys
                 85                  90                  95

Asp Val Lys Val Arg Asp Val Ile Leu Ala Met Thr Ser Thr Asp
                100                 105                 110
```

```
Ser Gln Met Asn Arg Val Ala Phe Gly Ser Val Asp Phe Ala Pro Cys
            115                 120                 125

Ala Asp Phe Glu Leu Leu Lys Asn Ala Tyr Asp Ala Ala Lys Asp Lys
130                 135                 140

Gly Val Pro Val Thr Val Gly Ser Val Phe Thr Ala Asp Gln Phe Tyr
145                 150                 155                 160

Asn Asp Asp Ser Gln Ile Glu Lys Leu Ala Lys Tyr Gly Val Leu Gly
                165                 170                 175

Val Glu Met Glu Thr Thr Ala Leu Tyr Thr Leu Ala Ala Lys His Gly
            180                 185                 190

Arg Lys Ala Leu Ser Ile Leu Thr Val Ser Asp His Val Leu Thr Gly
        195                 200                 205

Glu Glu Thr Thr Ala Glu Glu Arg Gln Thr Thr Phe His Asp Met Ile
    210                 215                 220

Glu Val Ala Leu His Ser Val Ser Gln
225                 230

<210> SEQ ID NO 9
<211> LENGTH: 816
<212> TYPE: DNA
<213> ORGANISM: Bacillus subtilis
<220> FEATURE:
<221> NAME/KEY: CDS
<222> LOCATION: (1)..(816)

<400> SEQUENCE: 9 ttg aag gac aga att gaa cgc gca gcc gct ttt att aaa caa aac ctg         48
Leu Lys Asp Arg Ile Glu Arg Ala Ala Ala Phe Ile Lys Gln Asn Leu
1               5                   10                  15 ccg gaa tct cca aag atc ggc ctt att tta ggc tca ggt ctt ggc att        96
Pro Glu Ser Pro Lys Ile Gly Leu Ile Leu Gly Ser Gly Leu Gly Ile
            20                  25                  30 ttg gcg gac gaa atc gaa aat ccg gtc aag ctg aaa tat gaa gat ata       144
Leu Ala Asp Glu Ile Glu Asn Pro Val Lys Leu Lys Tyr Glu Asp Ile
        35                  40                  45 cct gaa ttc ccg gta tct act gtt gaa ggg cat gcc gga cag ctt gtg       192
Pro Glu Phe Pro Val Ser Thr Val Glu Gly His Ala Gly Gln Leu Val
50                  55                  60 ctt ggc act ctt gaa gga gtt tcc gtc att gca atg cag ggc cgc ttt       240
Leu Gly Thr Leu Glu Gly Val Ser Val Ile Ala Met Gln Gly Arg Phe
65                  70                  75                  80 cat ttt tat gaa ggc tac tca atg gag aaa gtc aca ttc cct gta cgc       288
His Phe Tyr Glu Gly Tyr Ser Met Glu Lys Val Thr Phe Pro Val Arg
                85                  90                  95 gtg atg aaa gcg ctc ggt gtg gaa gcg ttg atc gtg aca aat gcc gca       336
Val Met Lys Ala Leu Gly Val Glu Ala Leu Ile Val Thr Asn Ala Ala
            100                 105                 110 ggc ggt gtc aac act gaa ttc cgt gcg gga gat tta atg att att acc       384
Gly Gly Val Asn Thr Glu Phe Arg Ala Gly Asp Leu Met Ile Ile Thr
        115                 120                 125 gat cat atc aac ttt atg gga aca aac ccg tta atc ggg cca aac gaa       432
Asp His Ile Asn Phe Met Gly Thr Asn Pro Leu Ile Gly Pro Asn Glu
    130                 135                 140 gca gat ttc ggc gcc aga ttt cca gat atg tct tca gcc tat gac aaa       480
Ala Asp Phe Gly Ala Arg Phe Pro Asp Met Ser Ser Ala Tyr Asp Lys
145                 150                 155                 160 gat ctg tcc agc ctg gct gaa aag att gcg aaa gac ctt aat atc cca       528
Asp Leu Ser Ser Leu Ala Glu Lys Ile Ala Lys Asp Leu Asn Ile Pro
                165                 170                 175
```

```
att caa aaa ggc gtg tac act gct gtg aca gga cct tct tac gaa aca    576
Ile Gln Lys Gly Val Tyr Thr Ala Val Thr Gly Pro Ser Tyr Glu Thr
        180                 185                 190 ccg gca gaa gtc cgt ttc tta aga acg atg ggc tct gat gca gtc ggc    624
Pro Ala Glu Val Arg Phe Leu Arg Thr Met Gly Ser Asp Ala Val Gly
    195                 200                 205 atg tct act gtt ccg gaa gtc att gta gcg aat cat gcg gga atg cgg    672
Met Ser Thr Val Pro Glu Val Ile Val Ala Asn His Ala Gly Met Arg
210                 215                 220 gtt ctt ggc att tcc tgc atc tct aac gcg gca gcc gga att ctg gat    720
Val Leu Gly Ile Ser Cys Ile Ser Asn Ala Ala Ala Gly Ile Leu Asp
225                 230                 235                 240 cag cct tta agt cac gat gaa gtt atg gaa gtg acc gaa aaa gta aaa    768
Gln Pro Leu Ser His Asp Glu Val Met Glu Val Thr Glu Lys Val Lys
            245                 250                 255 gct gga ttc tta aag ctt gtt aaa gcg atc gtc gct cag tac gaa taa    816
Ala Gly Phe Leu Lys Leu Val Lys Ala Ile Val Ala Gln Tyr Glu
        260                 265                 270

<210> SEQ ID NO 10
<211> LENGTH: 271
<212> TYPE: PRT
<213> ORGANISM: Bacillus subtilis

<400> SEQUENCE: 10

Leu Lys Asp Arg Ile Glu Arg Ala Ala Ala Phe Ile Lys Gln Asn Leu
1               5                   10                  15

Pro Glu Ser Pro Lys Ile Gly Leu Ile Leu Gly Ser Gly Leu Gly Ile
            20                  25                  30

Leu Ala Asp Glu Ile Glu Asn Pro Val Lys Leu Lys Tyr Glu Asp Ile
        35                  40                  45

Pro Glu Phe Pro Val Ser Thr Val Glu Gly His Ala Gly Gln Leu Val
    50                  55                  60

Leu Gly Thr Leu Glu Gly Val Ser Val Ile Ala Met Gln Gly Arg Phe
65                  70                  75                  80

His Phe Tyr Glu Gly Tyr Ser Met Glu Lys Val Thr Phe Pro Val Arg
                85                  90                  95

Val Met Lys Ala Leu Gly Val Glu Ala Leu Ile Val Thr Asn Ala Ala
            100                 105                 110

Gly Gly Val Asn Thr Glu Phe Arg Ala Gly Asp Leu Met Ile Ile Thr
        115                 120                 125

Asp His Ile Asn Phe Met Gly Thr Asn Pro Leu Ile Gly Pro Asn Glu
    130                 135                 140

Ala Asp Phe Gly Ala Arg Phe Pro Asp Met Ser Ser Ala Tyr Asp Lys
145                 150                 155                 160

Asp Leu Ser Ser Leu Ala Glu Lys Ile Ala Lys Asp Leu Asn Ile Pro
                165                 170                 175

Ile Gln Lys Gly Val Tyr Thr Ala Val Thr Gly Pro Ser Tyr Glu Thr
            180                 185                 190

Pro Ala Glu Val Arg Phe Leu Arg Thr Met Gly Ser Asp Ala Val Gly
        195                 200                 205

Met Ser Thr Val Pro Glu Val Ile Val Ala Asn His Ala Gly Met Arg
    210                 215                 220

Val Leu Gly Ile Ser Cys Ile Ser Asn Ala Ala Ala Gly Ile Leu Asp
225                 230                 235                 240

Gln Pro Leu Ser His Asp Glu Val Met Glu Val Thr Glu Lys Val Lys
                245                 250                 255
```

```
                                Ala Gly Phe Leu Lys Leu Val Lys Ala Ile Val Ala Gln Tyr Glu
                                        260                 265                 270

<210> SEQ ID NO 11
<211> LENGTH: 1293
<212> TYPE: DNA
<213> ORGANISM: Bacillus subtilis
<220> FEATURE:
<221> NAME/KEY: CDS
<222> LOCATION: (1)..(1293)

<400> SEQUENCE: 11 atg tct tca gta gtt gta gta ggt acg caa tgg ggc gat gaa gga aaa          48
Met Ser Ser Val Val Val Val Gly Thr Gln Trp Gly Asp Glu Gly Lys
1               5                   10                  15 ggt aaa att aca gat ttc cta tca gaa aat gca gaa gtg atc gcc cgt         96
Gly Lys Ile Thr Asp Phe Leu Ser Glu Asn Ala Glu Val Ile Ala Arg
                20                  25                  30 tat caa ggc gga aat aac gca ggg cat aca atc aag ttt gac gga atc        144
Tyr Gln Gly Gly Asn Asn Ala Gly His Thr Ile Lys Phe Asp Gly Ile
            35                  40                  45 aca tat aag ctt cac tta atc ccg tct gga att ttc tat aag gat aaa        192
Thr Tyr Lys Leu His Leu Ile Pro Ser Gly Ile Phe Tyr Lys Asp Lys
        50                  55                  60 acg tgt gta atc gga aac gga atg gtt gta gat ccg aaa gca tta gtc        240
Thr Cys Val Ile Gly Asn Gly Met Val Val Asp Pro Lys Ala Leu Val
65                  70                  75                  80 aca gag ctt gcg tat ctt cat gag cgc aac gtg agt aca gat aac ctg        288
Thr Glu Leu Ala Tyr Leu His Glu Arg Asn Val Ser Thr Asp Asn Leu
                85                  90                  95 aga atc agc aac aga gct cac gtc att ctg ccg tat cat ttg aaa ttg        336
Arg Ile Ser Asn Arg Ala His Val Ile Leu Pro Tyr His Leu Lys Leu
            100                 105                 110 gat gaa gtg gaa gaa gag cgt aaa ggg gct aac aag atc ggc aca acg        384
Asp Glu Val Glu Glu Glu Arg Lys Gly Ala Asn Lys Ile Gly Thr Thr
        115                 120                 125 aaa aaa gga atc ggc cct gct tac atg gat aaa gca gcc cgc atc gga        432
Lys Lys Gly Ile Gly Pro Ala Tyr Met Asp Lys Ala Ala Arg Ile Gly
130                 135                 140 att cgc atc gcg gat ctg tta gac cgt gac gcg ttt gcg gaa aag ctt        480
Ile Arg Ile Ala Asp Leu Leu Asp Arg Asp Ala Phe Ala Glu Lys Leu
145                 150                 155                 160 gag cgc aat ctt gaa gaa aaa aac cgt ctt ctc gag aaa atg tac gag        528
Glu Arg Asn Leu Glu Glu Lys Asn Arg Leu Leu Glu Lys Met Tyr Glu
                165                 170                 175 aca gaa ggg ttt aaa ctt gag gat atc tta gac gaa tat tat gag tac        576
Thr Glu Gly Phe Lys Leu Glu Asp Ile Leu Asp Glu Tyr Tyr Glu Tyr
            180                 185                 190 gga cag cag att aaa aag tat gtt tgc gat aca tct gtt gtc tta aac        624
Gly Gln Gln Ile Lys Lys Tyr Val Cys Asp Thr Ser Val Val Leu Asn
        195                 200                 205 gat gct ctt gat gaa ggg cgc cgt gta tta ttt gaa ggc gca caa ggg        672
Asp Ala Leu Asp Glu Gly Arg Arg Val Leu Phe Glu Gly Ala Gln Gly
    210                 215                 220 gtt atg ctc gat atc gac caa gga aca tac ccg ttt gtt acg tca tct        720
Val Met Leu Asp Ile Asp Gln Gly Thr Tyr Pro Phe Val Thr Ser Ser
225                 230                 235                 240 aac ccg gtt gcc ggc ggt gtc acg atc ggt tct ggt gtc ggc ccg acc        768
Asn Pro Val Ala Gly Gly Val Thr Ile Gly Ser Gly Val Gly Pro Thr
                245                 250                 255 aaa atc aag cac gtt gtc ggt gta tca aaa gca tat acg act cgt gtc        816
Lys Ile Lys His Val Val Gly Val Ser Lys Ala Tyr Thr Thr Arg Val
            260                 265                 270
```

```
                    260                 265                 270
ggc gac ggt cct ttt ccg act gag ctg aaa gat gaa atc ggc gat caa       864
Gly Asp Gly Pro Phe Pro Thr Glu Leu Lys Asp Glu Ile Gly Asp Gln
            275                 280                 285 atc cgt gaa gtc gga cgc gaa tat gga aca aca aca ggc cgc ccg cgc       912
Ile Arg Glu Val Gly Arg Glu Tyr Gly Thr Thr Thr Gly Arg Pro Arg
        290                 295                 300 cgt gtc ggc tgg ttt gac agc gtt gtt gtc cgc cac gcc cgc cgt gtg       960
Arg Val Gly Trp Phe Asp Ser Val Val Val Arg His Ala Arg Arg Val
305                 310                 315                 320 agc gga att aca gat ctt tct ctg aac tca att gac gtc cta gca gga      1008
Ser Gly Ile Thr Asp Leu Ser Leu Asn Ser Ile Asp Val Leu Ala Gly
                325                 330                 335 att gaa acg ttg aaa atc tgt gtg gcg tac cgc tac aaa ggc gaa atc      1056
Ile Glu Thr Leu Lys Ile Cys Val Ala Tyr Arg Tyr Lys Gly Glu Ile
            340                 345                 350 att gaa gaa ttc cca gca agt ctt aag gca ctt gct gaa tgt gag ccg      1104
Ile Glu Glu Phe Pro Ala Ser Leu Lys Ala Leu Ala Glu Cys Glu Pro
        355                 360                 365 gta tat gaa gaa atg ccg ggc tgg act gag gat att aca ggt gcg aag      1152
Val Tyr Glu Glu Met Pro Gly Trp Thr Glu Asp Ile Thr Gly Ala Lys
370                 375                 380 agc ttg agc gag ctt ccg gaa aat gcg cgc cat tat ctt gag cgt gtg      1200
Ser Leu Ser Glu Leu Pro Glu Asn Ala Arg His Tyr Leu Glu Arg Val
385                 390                 395                 400 tct cag ctg aca ggc att ccg ctt tct att ttc tct gtc ggt cca gac      1248
Ser Gln Leu Thr Gly Ile Pro Leu Ser Ile Phe Ser Val Gly Pro Asp
                405                 410                 415 cgc tca caa aca aat gtc ctt cgc agt gtg tac cgt gcg aac taa          1293
Arg Ser Gln Thr Asn Val Leu Arg Ser Val Tyr Arg Ala Asn
            420                 425                 430

<210> SEQ ID NO 12
<211> LENGTH: 430
<212> TYPE: PRT
<213> ORGANISM: Bacillus subtilis

<400> SEQUENCE: 12

Met Ser Ser Val Val Val Gly Thr Gln Trp Gly Asp Glu Gly Lys
1               5                   10                  15

Gly Lys Ile Thr Asp Phe Leu Ser Glu Asn Ala Glu Val Ile Ala Arg
            20                  25                  30

Tyr Gln Gly Gly Asn Asn Ala Gly His Thr Ile Lys Phe Asp Gly Ile
        35                  40                  45

Thr Tyr Lys Leu His Leu Ile Pro Ser Gly Ile Phe Tyr Lys Asp Lys
    50                  55                  60

Thr Cys Val Ile Gly Asn Gly Met Val Val Asp Pro Lys Ala Leu Val
65                  70                  75                  80

Thr Glu Leu Ala Tyr Leu His Glu Arg Asn Val Ser Thr Asp Asn Leu
                85                  90                  95

Arg Ile Ser Asn Arg Ala His Val Ile Leu Pro Tyr His Leu Lys Leu
            100                 105                 110

Asp Glu Val Glu Glu Glu Arg Lys Gly Ala Asn Lys Ile Gly Thr Thr
        115                 120                 125

Lys Lys Gly Ile Gly Pro Ala Tyr Met Asp Lys Ala Ala Arg Ile Gly
    130                 135                 140

Ile Arg Ile Ala Asp Leu Leu Asp Arg Asp Ala Phe Ala Glu Lys Leu
145                 150                 155                 160
```

```
Glu Arg Asn Leu Glu Glu Lys Asn Arg Leu Leu Glu Lys Met Tyr Glu
                165                 170                 175

Thr Glu Gly Phe Lys Leu Glu Asp Ile Leu Asp Glu Tyr Tyr Glu Tyr
            180                 185                 190

Gly Gln Gln Ile Lys Lys Tyr Val Cys Asp Thr Ser Val Val Leu Asn
        195                 200                 205

Asp Ala Leu Asp Glu Gly Arg Arg Val Leu Phe Glu Gly Ala Gln Gly
    210                 215                 220

Val Met Leu Asp Ile Asp Gln Gly Thr Tyr Pro Phe Val Thr Ser Ser
225                 230                 235                 240

Asn Pro Val Ala Gly Val Thr Ile Gly Ser Gly Val Gly Pro Thr
                245                 250                 255

Lys Ile Lys His Val Val Gly Val Ser Lys Ala Tyr Thr Thr Arg Val
                260                 265                 270

Gly Asp Gly Pro Phe Pro Thr Glu Leu Lys Asp Glu Ile Gly Asp Gln
            275                 280                 285

Ile Arg Glu Val Gly Arg Glu Tyr Gly Thr Thr Thr Gly Arg Pro Arg
        290                 295                 300

Arg Val Gly Trp Phe Asp Ser Val Val Arg His Ala Arg Val
305                 310                 315                 320

Ser Gly Ile Thr Asp Leu Ser Leu Asn Ser Ile Asp Val Leu Ala Gly
                325                 330                 335

Ile Glu Thr Leu Lys Ile Cys Val Ala Tyr Arg Tyr Lys Gly Glu Ile
                340                 345                 350

Ile Glu Glu Phe Pro Ala Ser Leu Lys Ala Leu Ala Glu Cys Glu Pro
            355                 360                 365

Val Tyr Glu Glu Met Pro Gly Trp Thr Glu Asp Ile Thr Gly Ala Lys
    370                 375                 380

Ser Leu Ser Glu Leu Pro Glu Asn Ala Arg His Tyr Leu Glu Arg Val
385                 390                 395                 400

Ser Gln Leu Thr Gly Ile Pro Leu Ser Ile Phe Ser Val Gly Pro Asp
                405                 410                 415

Arg Ser Gln Thr Asn Val Leu Arg Ser Val Tyr Arg Ala Asn
            420                 425                 430

<210> SEQ ID NO 13
<211> LENGTH: 1542
<212> TYPE: DNA
<213> ORGANISM: Bacillus subtilis
<220> FEATURE:
<221> NAME/KEY: CDS
<222> LOCATION: (1)..(1542)

<400> SEQUENCE: 13 atg tgg gaa agt aaa ttt tca aaa gaa ggc tta acg ttc gac gat gtg    48
Met Trp Glu Ser Lys Phe Ser Lys Glu Gly Leu Thr Phe Asp Asp Val
1               5                  10                  15 ctg ctt gtg cca gca aag tct gag gta ctt ccg cat gat gtg gat tta    96
Leu Leu Val Pro Ala Lys Ser Glu Val Leu Pro His Asp Val Asp Leu
            20                  25                  30 tct gta gaa ctt aca aaa acg tta aag cta aat att cct gtc atc agc   144
Ser Val Glu Leu Thr Lys Thr Leu Lys Leu Asn Ile Pro Val Ile Ser
        35                  40                  45 gca ggt atg gac act gta aca gaa tca gca atg gca att gca atg gca   192
Ala Gly Met Asp Thr Val Thr Glu Ser Ala Met Ala Ile Ala Met Ala
    50                  55                  60 aga cag ggc ggc ttg ggc atc att cac aaa aat atg tcc att gaa cag   240
Arg Gln Gly Gly Leu Gly Ile Ile His Lys Asn Met Ser Ile Glu Gln
65                  70                  75                  80
```

-continued

```
            65                  70                  75                  80
cag gct gaa caa gtt gat aaa gta aag cgt tct gag cgc ggc gtt atc        288
Gln Ala Glu Gln Val Asp Lys Val Lys Arg Ser Glu Arg Gly Val Ile
                    85                  90                  95 aca aat ccc ttc ttt tta act cct gat cac caa gta ttt gat gcg gag        336
Thr Asn Pro Phe Phe Leu Thr Pro Asp His Gln Val Phe Asp Ala Glu
            100                 105                 110 cat ttg atg ggg aaa tac aga att tcc ggt gtt ccg att gta aat aac        384
His Leu Met Gly Lys Tyr Arg Ile Ser Gly Val Pro Ile Val Asn Asn
            115                 120                 125 gaa gaa gac cag aag ctt gtt gga att att aca aac cgt gac ctt cgt        432
Glu Glu Asp Gln Lys Leu Val Gly Ile Ile Thr Asn Arg Asp Leu Arg
        130                 135                 140 ttt att tct gac tac tca atg aaa atc agc gac gtc atg acg aaa gaa        480
Phe Ile Ser Asp Tyr Ser Met Lys Ile Ser Asp Val Met Thr Lys Glu
145                 150                 155                 160 gag cta gtt act gca tct gta gga act act ctg gat gaa gct gaa aag        528
Glu Leu Val Thr Ala Ser Val Gly Thr Thr Leu Asp Glu Ala Glu Lys
                    165                 170                 175 att ttg caa aaa cat aaa att gaa aag ctt cct ctc gta gat gac cag        576
Ile Leu Gln Lys His Lys Ile Glu Lys Leu Pro Leu Val Asp Asp Gln
            180                 185                 190 aat aaa tta aaa ggt ctt atc aca att aaa gac att gaa aaa gtc att        624
Asn Lys Leu Lys Gly Leu Ile Thr Ile Lys Asp Ile Glu Lys Val Ile
            195                 200                 205 gag ttc ccg aac tca tct aaa gac att cac ggc cgc ctg atc gtt ggc        672
Glu Phe Pro Asn Ser Ser Lys Asp Ile His Gly Arg Leu Ile Val Gly
        210                 215                 220 gcg gca gtt ggt gta act ggc gat aca atg act cgc gtc aaa aag ctt        720
Ala Ala Val Gly Val Thr Gly Asp Thr Met Thr Arg Val Lys Lys Leu
225                 230                 235                 240 gtt gaa gcc aat gtt gat gtg att gtt atc gat aca gct cac gga cac        768
Val Glu Ala Asn Val Asp Val Ile Val Ile Asp Thr Ala His Gly His
                    245                 250                 255 tct caa ggc gtt tta aac aca gtt aca aaa atc cgt gaa acg tat ccc        816
Ser Gln Gly Val Leu Asn Thr Val Thr Lys Ile Arg Glu Thr Tyr Pro
            260                 265                 270 gaa tta aac att att gct gga aac gtg gca aca gct gaa gcg aca aga        864
Glu Leu Asn Ile Ile Ala Gly Asn Val Ala Thr Ala Glu Ala Thr Arg
            275                 280                 285 gcg ctt atc gaa gct gga gca gac gtt gtc aaa gtt gga ata ggg cct        912
Ala Leu Ile Glu Ala Gly Ala Asp Val Val Lys Val Gly Ile Gly Pro
        290                 295                 300 ggt tca att tgt act aca cgt gtt gta gcc ggg gtg ggt gtt ccg caa        960
Gly Ser Ile Cys Thr Thr Arg Val Val Ala Gly Val Gly Val Pro Gln
305                 310                 315                 320 att aca gca att tat gat tgt gcg act gaa gca aga aaa cac ggc aaa       1008
Ile Thr Ala Ile Tyr Asp Cys Ala Thr Glu Ala Arg Lys His Gly Lys
                    325                 330                 335 aca atc atc gcc gac ggt ggg att aaa ttc tct ggc gat atc act aaa       1056
Thr Ile Ile Ala Asp Gly Gly Ile Lys Phe Ser Gly Asp Ile Thr Lys
            340                 345                 350 gca ttg gca gcc ggc gga cat gct gtt atg ctc gga agc ttg ctt gca       1104
Ala Leu Ala Ala Gly Gly His Ala Val Met Leu Gly Ser Leu Leu Ala
            355                 360                 365 ggc aca tca gaa agc cct ggt gaa act gaa atc tac caa ggc aga aga       1152
Gly Thr Ser Glu Ser Pro Gly Glu Thr Glu Ile Tyr Gln Gly Arg Arg
        370                 375                 380 ttt aag gta tac cgc ggc atg gga tca gtt gct gca atg gaa aaa gga       1200
Phe Lys Val Tyr Arg Gly Met Gly Ser Val Ala Ala Met Glu Lys Gly
```

```
                385             390             395             400
agt aaa gac cgt tac ttc caa gaa gaa aac aaa aaa ttt gtt cct gaa   1248
Ser Lys Asp Arg Tyr Phe Gln Glu Glu Asn Lys Lys Phe Val Pro Glu
                405                 410                 415 gga att gaa gga cgc aca cct tac aaa ggg cca gtt gaa gaa acc gtt   1296
Gly Ile Glu Gly Arg Thr Pro Tyr Lys Gly Pro Val Glu Glu Thr Val
                420                 425                 430 tat cag cta gtc gga ggc ctt cgt tct ggt atg ggg tat tgc ggg tcc   1344
Tyr Gln Leu Val Gly Gly Leu Arg Ser Gly Met Gly Tyr Cys Gly Ser
            435                 440                 445 aaa gat ctg cgt gcg cta aga gaa gaa gct cag ttc att cgc atg act   1392
Lys Asp Leu Arg Ala Leu Arg Glu Glu Ala Gln Phe Ile Arg Met Thr
        450                 455                 460 ggc gca gga ctt cgc gaa agc cat ccg cat gac gta cag att aca gtg   1440
Gly Ala Gly Leu Arg Glu Ser His Pro His Asp Val Gln Ile Thr Val
465                 470                 475                 480 cat cgt aat aag gcg ctt cct ggt cta ttt ggt tct cat cag aaa aaa   1488
His Arg Asn Lys Ala Leu Pro Gly Leu Phe Gly Ser His Gln Lys Lys
                485                 490                 495 aca gga ttt gtg tat gat gaa tgt tgt caa tcc ggc ttt ttt tca tcg   1536
Thr Gly Phe Val Tyr Asp Glu Cys Cys Gln Ser Gly Phe Phe Ser Ser
                500                 505                 510 gat tga                                                            1542
Asp

<210> SEQ ID NO 14
<211> LENGTH: 513
<212> TYPE: PRT
<213> ORGANISM: Bacillus subtilis

<400> SEQUENCE: 14

Met Trp Glu Ser Lys Phe Ser Lys Glu Gly Leu Thr Phe Asp Asp Val
1               5                   10                  15

Leu Leu Val Pro Ala Lys Ser Glu Val Leu Pro His Asp Val Asp Leu
                20                  25                  30

Ser Val Glu Leu Thr Lys Thr Leu Lys Leu Asn Ile Pro Val Ile Ser
            35                  40                  45

Ala Gly Met Asp Thr Val Thr Glu Ser Ala Met Ala Ile Ala Met Ala
        50                  55                  60

Arg Gln Gly Gly Leu Gly Ile Ile His Lys Asn Met Ser Ile Glu Gln
65                  70                  75                  80

Gln Ala Glu Gln Val Asp Lys Val Lys Arg Ser Glu Arg Gly Val Ile
                85                  90                  95

Thr Asn Pro Phe Phe Leu Thr Pro Asp His Gln Val Phe Asp Ala Glu
                100                 105                 110

His Leu Met Gly Lys Tyr Arg Ile Ser Gly Val Pro Ile Val Asn Asn
            115                 120                 125

Glu Glu Asp Gln Lys Leu Val Gly Ile Ile Thr Asn Arg Asp Leu Arg
        130                 135                 140

Phe Ile Ser Asp Tyr Ser Met Lys Ile Ser Asp Val Met Thr Lys Glu
145                 150                 155                 160

Glu Leu Val Thr Ala Ser Val Gly Thr Thr Leu Asp Glu Ala Glu Lys
                165                 170                 175

Ile Leu Gln Lys His Lys Ile Glu Lys Leu Pro Leu Val Asp Asp Gln
            180                 185                 190

Asn Lys Leu Lys Gly Leu Ile Thr Ile Lys Asp Ile Glu Lys Val Ile
        195                 200                 205
```

```
Glu Phe Pro Asn Ser Ser Lys Asp Ile His Gly Arg Leu Ile Val Gly
    210                 215                 220

Ala Ala Val Gly Val Thr Gly Asp Thr Met Thr Arg Val Lys Lys Leu
225                 230                 235                 240

Val Glu Ala Asn Val Asp Val Ile Val Ile Asp Thr Ala His Gly His
                245                 250                 255

Ser Gln Gly Val Leu Asn Thr Val Thr Lys Ile Arg Glu Thr Tyr Pro
            260                 265                 270

Glu Leu Asn Ile Ile Ala Gly Asn Val Ala Thr Ala Glu Ala Thr Arg
        275                 280                 285

Ala Leu Ile Glu Ala Gly Ala Asp Val Val Lys Val Gly Ile Gly Pro
    290                 295                 300

Gly Ser Ile Cys Thr Thr Arg Val Val Ala Gly Val Gly Val Pro Gln
305                 310                 315                 320

Ile Thr Ala Ile Tyr Asp Cys Ala Thr Glu Ala Arg Lys His Gly Lys
                325                 330                 335

Thr Ile Ile Ala Asp Gly Gly Ile Lys Phe Ser Gly Asp Ile Thr Lys
            340                 345                 350

Ala Leu Ala Ala Gly Gly His Ala Val Met Leu Gly Ser Leu Leu Ala
        355                 360                 365

Gly Thr Ser Glu Ser Pro Gly Glu Thr Glu Ile Tyr Gln Gly Arg Arg
    370                 375                 380

Phe Lys Val Tyr Arg Gly Met Gly Ser Val Ala Ala Met Glu Lys Gly
385                 390                 395                 400

Ser Lys Asp Arg Tyr Phe Gln Glu Glu Asn Lys Lys Phe Val Pro Glu
                405                 410                 415

Gly Ile Glu Gly Arg Thr Pro Tyr Lys Gly Pro Val Glu Glu Thr Val
            420                 425                 430

Tyr Gln Leu Val Gly Gly Leu Arg Ser Gly Met Gly Tyr Cys Gly Ser
        435                 440                 445

Lys Asp Leu Arg Ala Leu Arg Glu Glu Ala Gln Phe Ile Arg Met Thr
    450                 455                 460

Gly Ala Gly Leu Arg Glu Ser His Pro His Asp Val Gln Ile Thr Val
465                 470                 475                 480

His Arg Asn Lys Ala Leu Pro Gly Leu Phe Gly Ser His Gln Lys Lys
                485                 490                 495

Thr Gly Phe Val Tyr Asp Glu Cys Cys Gln Ser Gly Phe Phe Ser Ser
            500                 505                 510

Asp

<210> SEQ ID NO 15
<211> LENGTH: 17
<212> TYPE: DNA
<213> ORGANISM: Artificial
<220> FEATURE:
<223> OTHER INFORMATION: primer

<400> SEQUENCE: 15
gaagttgatg atcaaaa                                                17

<210> SEQ ID NO 16
<211> LENGTH: 19
<212> TYPE: DNA
<213> ORGANISM: Artificial
<220> FEATURE:
<223> OTHER INFORMATION: primer

<400> SEQUENCE: 16
```

-continued

```
acatattgtt gacgataat                                          19

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
ttcccttagg gttattttcg tttcaaaa                                28

<210> SEQ ID NO 18
<211> LENGTH: 50
<212> TYPE: DNA
<213> ORGANISM: Artificial
<220> FEATURE:
<223> OTHER INFORMATION: primer

<400> SEQUENCE: 18
cgtttgttga actaatgggt gcttttatga gcatgtgcat gataaggtga        50

<210> SEQ ID NO 19
<211> LENGTH: 50
<212> TYPE: DNA
<213> ORGANISM: Artificial
<220> FEATURE:
<223> OTHER INFORMATION: primer

<400> SEQUENCE: 19
acagctccag atccatatcc ttctttttta gagagtttgc gggagtatcg        50

<210> SEQ ID NO 20
<211> LENGTH: 27
<212> TYPE: DNA
<213> ORGANISM: Artificial
<220> FEATURE:
<223> OTHER INFORMATION: primer

<400> SEQUENCE: 20
taaaggtttt tcgggataag attgaaa                                 27

<210> SEQ ID NO 21
<211> LENGTH: 50
<212> TYPE: DNA
<213> ORGANISM: Artificial
<220> FEATURE:
<223> OTHER INFORMATION: primer

<400> SEQUENCE: 21
tcaccttatc atgcacatgc tcataaaagc acccattagt tcaacaaacg        50

<210> SEQ ID NO 22
<211> LENGTH: 50
<212> TYPE: DNA
<213> ORGANISM: Artificial
<220> FEATURE:
<223> OTHER INFORMATION: primer

<400> SEQUENCE: 22
cgatactccc gcaaactctc taaaaaagaa ggatatggat ctggagctgt        50
```

PURINE-DERIVED SUBSTANCE-PRODUCING BACTERIUM AND A METHOD FOR PRODUCING A PURINE-DERIVED SUBSTANCE

This application is a continuation under 35 U.S.C. §120 to PCT Patent Application No. PCT/JP2007/058356, filed on Apr. 17, 2007, which claims priority under 35 U.S.C. §119 to Japanese Patent Application No. 2006-119315, filed Apr. 24, 2006, both of which are incorporated by reference. The Sequence Listing in electronic format filed herewith is also hereby incorporated by reference in its entirety (File Name: US-376_Seq_List; File Size: 63 KB; Date Created Oct. 21, 2008).

BACKGROUND OF THE INVENTION

1. Technical Field

The present invention relates to a method for producing purine-derived substances such as purine nucleotides and purine nucleosides. Purine nucleotides typically include 5'-inosinic acid and 5'-guanylic acid, and purine nucleosides typically include inosine and guanosine. Purine nucleosides are important for their use as starting materials for the synthesis of purine nucleotides, and so forth. *Bacillus* bacteria can be used in the methods described herein. Purine-derived substances are useful as seasonings, drugs, raw materials thereof, and so forth.

2. Background Art

Methods for producing inosine and guanosine by fermentation using adenine auxotrophic strains of *Bacillus* bacteria have been reported. Derivatives of these bacteria which are made resistant to various drugs such as purine analogues have also been reported (Japanese Patent Publication (KOKOKU) No. 38-23099, Japanese Patent Publication No. 54-17033, Japanese Patent Publication No. 55-2956, Japanese Patent Publication No. 55-45199, Japanese Patent Publication No. 57-14160, Japanese Patent Publication No. 57-41915, Japanese Patent Laid-open (KOKAI) No. 59-42895, and Japanese Patent Laid-open No. 2004-242610). Microorganisms of the genus *Brevibacterium* have also been reported to be useful for production of inosine and guanosine by fermentation (Japanese Patent Publication No. 51-5075, Japanese Patent Publication No. 58-17592, and Agric. Biol. Chem., 1978, 42, 399-405.

Such mutant strains are typically obtained by treating the microorganism with ultraviolet irradiation or nitrosoguanidine (N-methyl-N'-nitro-N-nitrosoguanidine), and selecting the mutant with the desired properties using a suitable selection medium.

Furthermore, strains which produce purine-derived substances have also been bred using genetic engineering techniques in *Bacillus* bacteria (Japanese Patent Laid-open No. 58-158197, Japanese Patent Laid-open No. 58-175493, Japanese Patent Laid-open No. 59-28470, Japanese Patent Laid-open No. 60-156388, Japanese Patent Laid-open No. 1-27477, Japanese Patent Laid-open No. 1-174385, Japanese Patent Laid-open No. 3-58787, Japanese Patent Laid-open No. 3-164185, Japanese Patent Laid-open No. 5-84067, and Japanese Patent Laid-open No. 5-192164), *Brevibacterium* bacteria (Japanese Patent Laid-open No. 63-248394), and *Escherichia* bacteria (International Patent Publication WO99/03988). Specifically, for example, a method for efficiently producing nucleic acid-derived compounds such as hypoxanthine, uracil, guanine, and adenine with a *Bacillus* bacterium in which the gene (purR) encoding the purine operon repressor is disrupted has been disclosed (U.S. Pat. No. 6,284,495).

In *Bacillus subtilis*, the purine operon repressor as described above is known to regulate the genes of the purine operon. The purine operon repressor also regulates the purA gene, which is involved in AMP biosynthesis (Proc. Natl. Acad. Sci. USA, 1995, 92, 7455-7459), the glyA gene, which is involved in formyltetrahydrofolic acid biosynthesis (J. Bacteriol., 2001, 183, 6175-6183), the pbuG gene, which encodes the transporter of hypoxanthine/guanine (J. Bacteriol., 2003, 185, 5200-5209), and so forth.

Furthermore, a microorganism which is made auxotrophic for adenine by disruption of the succinyl-AMP synthase (purA) and purR genes, and suppression of the decomposition of inosine into hypoxanthine by disruption of the purine nucleoside phosphorylase gene (deoD), has also been reported, as well as a method for producing inosine using this microorganism (Japanese Patent Laid-open No. 2004-242610).

Fructose bisphosphatase is one of the gluconeogenic enzyme, which catalyzes the generation of fructose-6-phosphate from fructose-1,6-bisphosphate. There is not much known about the relationship between this enzyme and the biosynthetic pathway of purine-derived substances, and there have been no reports of an attempt to breed bacteria able to produce purine-derived substances by reducing the activity of this enzyme.

SUMMARY OF THE INVENTION

The present invention describes a *Bacillus* bacterium suitable for fermentative production of purine-derived substances such as purine nucleosides and/or purine nucleotides, and to provide a method for producing a purine-derived substance using such a bacterium.

It was found that when the enzymatic activity of fructose bisphosphatase of the glyconeogenesis pathway is decreased in a *Bacillus* bacterium, the ability of the bacterium to produce purine nucleosides or purine nucleotides is improved.

The present invention thus provides the following:

It is an aspect of the present invention to provide a bacterium belonging to the genus *Bacillus* which is able to produce a purine-derived substance, wherein the bacterium has been modified to decrease the enzymatic activity of fructose bisphosphatase.

It is a further aspect of the present invention to provide the bacterium as described above, wherein the purine-derived substance is a purine nucleoside selected from the group consisting of inosine, xanthosine, guanosine, and adenosine.

It is a further aspect of the present invention to provide the bacterium as described above, wherein the purine-derived substance is a purine nucleotide selected from the group consisting of inosinic acid, xanthylic acid, guanylic acid, and adenylic acid.

It is a further aspect of the present invention to provide the bacterium as described above, wherein the fructose bisphosphatase activity is decreased by disrupting the gene encoding fructose bisphosphatase.

It is a further aspect of the present invention to provide the bacterium as described above, wherein said gene encodes a protein selected from the group consisting of:

(A) a protein comprising the amino acid sequence of SEQ ID NO: 1, (B) a protein comprising the amino acid sequence of SEQ ID NO: 1, but which includes substitutions, deletions, insertions, additions or inversions of one or several amino acid residues and has fructose bisphosphatase activity, and (C) combinations thereof.

It is a further aspect of the present invention to provide the bacterium as described above, which has been further modified to increase phosphoribosyl pyrophosphate synthetase activity.

It is a further aspect of the present invention to provide the bacterium as described above, which has been further modified to increase expression of the purine operon.

It is a further aspect of the present invention to provide the bacterium as described above, wherein said expression is increased by disrupting the purR gene, wherein said purR gene encodes a repressor of the purine operon.

It is a further aspect of the present invention to provide the bacterium as described above, which has been further modified to decrease purine nucleoside phosphorylase activity.

It is a further aspect of the present invention to provide the bacterium as described above, which has been further modified to decrease IMP dehydrogenase activity.

It is a further aspect of the present invention to provide the bacterium as described above, which is *Bacillus subtilis*.

It is another aspect of the present invention to provide a method for producing a purine-derived substance, which comprises culturing the *Bacillus* bacterium as described above in a medium, and collecting the purine-derived substance from the bacterium or medium.

It is a further aspect of the present invention to provide the method as described above, wherein the purine-derived substance is a purine nucleoside or a purine nucleotide.

It is a further aspect of the present invention to provide the method as described above, wherein the purine-derived substance is a purine nucleoside selected from the group consisting of inosine, xanthosine, guano sine, and adeno sine.

It is a further aspect of the present invention to provide the method as described above, wherein the purine-derived substance is a purine nucleotide selected from the group consisting of inosinic acid, xanthylic acid, guanylic acid, and adenylic acid.

It is a further aspect of the present invention to provide a method for producing a purine nucleotide, which comprises (A) producing a purine nucleoside by the method as described above, (B) reacting the purine nucleoside with a phosphate donor selected from the group consisting of polyphosphoric acid, phenyl phosphate, and carbamyl phosphate, and a microorganism which is able to produce a nucleoside-5'-phosphoric acid ester or acid phosphatase to produce a purine nucleotide, and (C) collecting the purine nucleotide.

DESCRIPTION OF THE PREFERRED EMBODIMENTS

<1> *Bacillus* bacterium (I) Imparting the Ability to Produce a Purine-Derived Substance The phrase "activity is decreased" or "to decrease the activity" indicates that the activity is lower than the activity in an unmodified strain, such as a wild-type *Bacillus* bacterium. This phrase can also mean that the activity is substantially eliminated.

The *Bacillus* bacterium is able to produce a purine-derived substance and has been modified to decrease the enzymatic activity of fructose bisphosphatase.

The term "purine-derived substance" means a substance having a purine skeleton, and examples include purine nucleosides, purine nucleotides, and so forth. The purine nucleosides include inosine, xanthosine, guanosine, adenosine, and so forth, and the purine nucleotides include 5'-phosphoric acid esters of purine nucleosides, for example, inosinic acid (inosine-5'-phosphate, henceforth also referred to as "IMP"), xanthylic acid (xanthosine-5'-phosphate, henceforth also referred to as "XMP"), guanylic acid (guanosine-5'-monophosphate, henceforth also referred to as "GMP"), adenylic acid (adenosine-5'-monophosphate, henceforth also referred to as "AMP"), and so forth.

The phrase "ability to produce a purine-derived substance" or "is able to produce a purine-derived substance" means the ability of the *Bacillus* bacterium to produce, secrete, or cause accumulation of a purine-derived substance in the bacterial cells or the medium in which the bacterium is cultured to such an extent that the purine-derived substance can be collected from the cells or medium. The *Bacillus* bacterium may be able to produce two or more kinds of the aforementioned purine-derived substances.

The *Bacillus* bacterium which is able to produce a purine-derived substance may inherently have this ability, or may be modified as described below to have this ability. Bacteria may be modified by using a mutagenesis or recombinant DNA technique. Moreover, the *Bacillus* bacterium may be modified so that enzymatic activity of fructose bisphosphatase is decreased, in such a manner as described later.

The phrase "enzymatic activity is decreased" or "to decrease the enzymatic activity" indicates that the enzymatic activity of fructose bisphosphatase described above, or of an enzyme which decomposes a purine-derived substance such as inosine monophosphate (IMP) dehydrogenase, or the like is lower than that in an unmodified strain, for example, a wild-type strain of the *Bacillus* bacterium. This can also mean that the activity is substantially eliminated. The same shall apply to the activity of the purine operon repressor described later.

Examples of the *Bacillus* bacterium include *Bacillus subtilis*, *Bacillus amyloliquefaciens*, *Bacillus pumilus*, and so forth.

Examples of *Bacillus subtilis* include *Bacillus subtilis* 168 Marburg (ATCC 6051), *Bacillus subtilis* PY79 (Plasmid, 1984, 12, 1-9) and so forth, and examples of *Bacillus amyloliquefaciens* include *Bacillus amyloliquefaciens* T (ATCC 23842), *Bacillus amyloliquefaciens* N (ATCC 23845), and so forth. Examples of *Bacillus pumilus* include *Bacillus pumilus* Gottheil No. 3218 (ATCC No. 21005, U.S. Pat. No. 3,616, 206), and so forth. These strains can be obtained from the American Type Culture Collection (Address: P.O. Box 1549, Manassas, Va. 20108, United States of America).

A *Bacillus* bacterium which is able to produce a purine-derived substance can be obtained, for example, by making the bacteria auxotrophic for purine nucleosides or resistant to purine analogues (Japanese Patent Publication Nos. 38-23099, 54-17033, 55-45199, 57-14160, 57-41915 and 59-42895). A *Bacillus* bacterium which is auxotrophic or drug resistant can be obtained by treating the bacterium with a known mutagen such as N-methyl-N'-nitro-N-nitrosoguanidine (NTG) or EMS (ethyl methanesulfonate).

Examples of *Bacillus* bacteria which produce a purine nucleoside include the following. A *Bacillus* strain which is able to produce inosine is *Bacillus subtilis* KMBS16. This strain is derived from the known *Bacillus subtilis* trpC2 strain (168 Marburg) by disrupting the following genes: purR encoding the purine operon repressor (purR::spc), purA encoding succinyl-AMP synthase (purA::erm), and deoD encoding purine nucleoside phosphorylase (deoD::kan) (Japanese Patent Laid-open No. 2004-242610, US2004166575A1). *Bacillus subtilis* AJ3772 strain (FERM P-2555, Japanese Patent Laid-open No. 62-014794) and so forth may also be used.

Examples of *Bacillus* bacteria which is able to produce guanosine include a *Bacillus* bacterium with increased IMP dehydrogenase activity (Japanese Patent Laid-open No. 3-58787), a *Bacillus* bacterium which is obtained by introducing a vector containing a gene conferring resistance to a purine analogue or decoyinine into an adenine auxotrophic mutant (Japanese Patent Publication No. 4-28357), and so forth.

Examples of *Bacillus* bacteria which produce a purine nucleotide include the following. *Bacillus subtilis* which have attenuated phosphatase activity have been reported to be able to produce inosinic acid (Uchida, K. et al., Agr. Biol. Chem., 1961, 25, 804-805; Fujimoto, M., Uchida, K., Agr. Biol. Chem., 1965, 29, 249-259). Examples of *Bacillus* bacteria which are able to produce guanylic acid, including 5'-guanylic acid (guanosine-5'-monophosphate, henceforth referred to as "GMP"), include mutants of *Bacillus* bacteria which are auxotrophic for adenine, and resistant to decoyinine or methionine sulfoxide (Japanese Patent Publication No. 56-12438).

Furthermore, bacteria which are able to produce xanthylic acid can be constructed by known methods for breeding coryneform bacteria, typically including *Corynebacterium ammoniagenes*. For example, a strain able to produce xanthylic acid can be obtained enhancing PRPP amidotransferase (Japanese Patent Laid-open No. 8-168383), or making the strain resistant to aliphatic amino acids (Japanese Patent Laid-open No. 4-262790) or dehydroproline (South Korean Patent Unexamined Publication No. 2003-56490).

Moreover, another example of a method for breeding *Bacillus* bacteria which are able to produce purine-derived substances is to enhance the activities of enzymes involved in purine biosynthesis which are common to the biosynthesis of purine nucleosides and purine nucleotides, i.e., purine biosynthesis enzymes, in bacterial cells. The activity of the enzyme in the cells is preferably increased to a level greater than that of an unmodified strain of *Bacillus* bacterium, for example, a wild-type *Bacillus* bacterium. The phrase "activity is increased" includes, for example, when the number of enzyme molecules per cell is increased, and when the specific activity per enzyme molecule is increased, and so forth. For example, the activity can be increased by increasing the expression of the gene which encodes the enzyme.

Examples of enzymes involved in purine biosynthesis include, for example, phosphoribosyl pyrophosphate amidotransferase, phosphoribosyl pyrophosphate synthetase (PRPP synthetase [EC: 2.7.6.1]), and so forth.

Some of the catabolites produced by the metabolism of sugar sources such as glucose that flow into the pentose phosphate pathway are converted into ribose-5-phosphate via ribulose-5-phosphate. From the biosynthesized ribose-5-phosphate, PRPP is produced, which is an indispensable precursor for purine nucleoside, histidine, and tryptophan biosyntheses. Specifically, ribose-5-phosphate is converted into PRPP by phosphoribosyl pyrophosphate synthetase. Therefore, the ability to produce purine-derived substances can be imparted to a *Bacillus* bacterium by modifying the bacterium so that the activity of PRPP synthetase is increased.

The phrase "activity of phosphoribosyl pyrophosphate synthetase is increased" or "to increase phosphoribosyl pyrophosphate synthetase activity" means that the activity of phosphoribosyl pyrophosphate synthetase is increased as compared to that of an unmodified strain such as a wild-type strain or a parent strain. The activity of phosphoribosyl pyrophosphate synthetase can be measured by, for example, the method of Switzer et al. (Methods Enzymol., 1978, 51, 3-11) or Roth et al. (Methods Enzymol., 1978, 51, 12-17). A *Bacillus* bacterium in which the activity of phosphoribosyl pyrophosphate synthetase is increased can be obtained by, for example, increasing the expression of the gene encoding the phosphoribosyl pyrophosphate synthetase in the *Bacillus* bacterium by introducing a plasmid containing the gene or integrating the gene into the chromosome (Japanese Patent Laid-open No. 2004-242610). Although the prs gene (SEQ ID NO: 3) derived from a *Bacillus* bacterium (Genbank Accession No. X16518) encodes phosphoribosyl pyrophosphate synthetase and may be used, genes derived from other bacteria, animals, or plants which encode a protein having phosphoribosyl pyrophosphate synthetase activity may also be used.

Furthermore, once PRPP is produced, some of it is converted into purine nucleotides and purine nucleosides by the enzymes involved in the purine biosynthesis. Examples of the genes encoding such enzymes include the genes of the purine operon from *Bacillus subtilis*, specifically, genes of the purEKB-purC(orf) QLF-purMNH(J)-purD operon (Ebbole D. J. and Zalkin H., J. Biol. Chem., 1987, 262, 17, 8274-87) (at present, also called purEKBCSQLFMNHD, *Bacillus subtilis* and Its Closest Relatives, Editor in Chief: A. L. Sonenshein, ASM Press, Washington D.C., 2002, Genbank Accession No. NC_000964), and the genes of the pur regulon from *Escherichia coli* (*Escherichia* and *Salmonella*, Second Edition, Editor in Chief: F. C. Neidhardt, ASM Press, Washington D.C., 1996).

Accordingly, enhancing expression of these genes imparts or enhances the ability to produce a purine-derived substance. In addition, genes of the purine operon which can be used are not limited to these, and genes derived from other microorganisms, animals, and plants may also be used.

Examples of the method for increasing the expression of the purine operon include increasing the expression of genes of the purine operon in a *Bacillus* bacterium by introducing a plasmid containing the genes or integrating the genes into the chromosome, or the like.

The second method for increasing the expression of the purine operon is to replace the native promoter of the purine operon with a stronger one, and to replace the −35 or −10 region of the native promoter with a consensus sequence.

For example, in *Bacillus subtilis* (*B. subtilis* 168 Marburg strain, ATCC 6051), the −35 sequence of the purine operon is a consensus sequence (TTGACA), but the −10 sequence is TAAGAT, which differs from the consensus sequence TATAAT (Ebbole, D. J. and H. Zalikn, J. Biol. Chem., 1987, 262, 8274-8287). Therefore, by changing the −10 sequence (TAAGAT) to the similar consensus sequence TATAAT, TATGAT, or TAAAAT, the transcriptional activity of the purine operon can be increased. The promoter sequence can be replaced by the same method as that of the gene substitution, which is described below.

The third method for increasing the expression of the purine operon is to reduce the expression of the purine operon repressor (U.S. Pat. No. 6,284,495). The phrase "expression of the purine operon repressor" includes both the transcription of the purine operon gene and the translation of the transcription product. Furthermore, "expression is decreased" means when the expression is lower than that in an unmodified strain such as a wild-type *Bacillus* bacterium, and also when the expression is substantially eliminated.

Expression of the purine operon repressor (purine repressor) can be decreased by, for example, irradiating the *Bacillus* bacterium with ultraviolet rays or treating the bacterium with a known mutagen such as NTG or EMS, and selecting a mutant with decreased expression of the purine repressor.

Furthermore, a *Bacillus* bacterium with decreased expression of the purine repressor can also be obtained by, for example, besides a mutagenesis treatment, replacing the gene encoding the purine repressor on the chromosome (purR, GenBank Accession NC_000964, coding region corresponds to the nucleotide numbers 54439 to 55293, SEQ ID NO: 5) with a corresponding gene that does not function normally (hereinafter, also referred to as a "disrupted-type gene") by homologous recombination utilizing gene recombination techniques (Experiments in Molecular Genetics, Cold Spring Harbor Laboratory Press (1972); Matsuyama, S. and Mizushima, S., J. Bacteriol., 1985, 162, 1196-1202).

For example, the native gene can be replaced with a disrupted-type gene on the host chromosome in the manner as described below. Hereinafter, the disruption of the purR gene is described. Other genes such as purA, deoD, guaB and fbp can be similarly disrupted.

A plasmid which is not capable of replicating in the chosen host, such as *Bacillus* bacteria, or the like, is constructed to have a sequence which is homologous to a sequence on the chromosome of the *Bacillus* bacteria. When this plasmid is introduced into the bacterial cell, recombination at the site of the homologous sequence occurs at a certain frequency. The entire plasmid is then recombined into the chromosome. Thereafter, if further recombination occurs at the site of the homologous sequence, the plasmid is deleted from the chromosome. At this time, depending on the site where the recombination occurs, the disrupted-type gene may remain on the chromosome, and the original native gene may be deleted from the chromosome with the plasmid. By this method, a strain in which the native purR gene on the chromosome is replaced with the disrupted-type purR gene is obtained.

Disrupting genes using homologous recombination techniques is well known, and includes when linear DNA and/or a temperature sensitive plasmid is used, and so forth. Furthermore, the purR gene can also be disrupted by using a plasmid containing the purR gene and a marker gene, such as a drug resistance gene, and which is not able to replicate in the target bacterial cell. That is, in a cell that has been transformed with such a plasmid, the marker gene is incorporated into the chromosomal DNA and imparts drug resistance. Since the marker gene is incorporated into the chromosome at a high rate by homologous recombination of the purR gene sequences that sandwiches the marker gene on the plasmid with the purR gene on the chromosome, bacterial strains containing the disrupted purR gene can be selected efficiently.

The disrupted-type purR gene used for the gene disruption can be obtained by, specifically, deleting a particular region of the purR gene by digestion with a restriction enzyme and re-ligation, inserting another DNA fragment (marker gene etc.) into the purR gene, or substituting, deleting, inserting, adding, or inverting one or more nucleotides in the nucleotide sequence of the coding region, promoter region, or the like of the purR gene by site-specific mutagenesis (Kramer, W. and Frits, H. J., Methods in Enzymology, 1987, 154, 350-367) recombinant PCR(PCR Technology, Stockton Press (1989)) or treatment with a chemical agent such as sodium hyposulfite or hydroxylamine (Shortle, D. and Nathans, D., Proc. Natl. Acad. Sci. U.S.A., 1978, 75, 2170-2174). Then, the strain with decreased purR repressor activity or decreased purR gene transcription can be selected. Among these methods, either deleting a particular region of the purR gene by digestion with a restriction enzyme and re-ligation, or inserting another DNA fragment into the purR gene, is preferable in view of reliability and stability. The particular region of the purR gene to be deleted may be a 5' end sequence, internal sequence, or 3' end sequence. However, if the region includes 90% or more, more preferably 95% or more, particularly 97% or more, of the full length purR gene, it is more likely to ensure a reduction in repressor activity. Furthermore, when a frame shift mutation is caused by deletion or insertion of nucleotides in the coding region of the purR gene, it is preferable to delete or insert nucleotides at multiple sites on the 3' end, so as to ensure reduction of the repressor activity.

The purine repressor activity can also be reduced by, besides the aforementioned gene disruption, using well-known mutagenesis methods to introduce a mutation that reduces the intracellular purine repressor activity into the purR gene on the chromosome. For example, an amino acid substitution (missense mutation), a stop codon (nonsense mutation), or a frame shift mutation that adds or deletes one or two nucleotides can be introduced, or the gene can be partially or entirely deleted. Furthermore, the activity of the repressor can also be decreased by inserting a transposon into the purR gene on the chromosome.

The activity of the purine repressor can also be reduced by replacing an expression control sequence of the purR gene, such as promoter, on the chromosomal DNA with a weaker one. The strength of a promoter is defined by the frequency of initiation acts of RNA synthesis. Examples of method for evaluating the strength of promoters and strong promoters are described in the paper of Goldstein et al. (Prokaryotic promoters in biotechnology, Biotechnol. Annu. Rev., 1995, 1, 105-128), and so forth. Furthermore, several nucleotides in the promoter region of the target gene can be substituted with a nucleotide, resulting in a weaker promoter (International Patent Publication WO00/18935). Furthermore, it is known that several nucleotides in the spacer region between the ribosome binding site (RBS) and the start codon can be substituted, in particular, the sequence immediately upstream from the start codon, and as a result, the translation efficiency of the mRNA is greatly effected. This modification of the RBS may be combined with decreasing the transcription of the target gene.

Furthermore, a recombinant DNA may be prepared which contains a mutation that destabilizes the purR messenger RNA. This DNA can then be transformed into a host *Bacillus* bacterium.

The activities of the enzymes encoded by the purA, deoD, guaB, and fbp genes described later can also be decreased in the same manner as described above.

The purR gene can be obtained from the chromosomal DNA of a microorganism which contains the purine operon by PCR using oligonucleotide primers prepared based on the known nucleotide sequence of the purR gene. The purR gene can also be obtained from a chromosomal DNA library of a microorganism which contains the purine operon by hybridization using an oligonucleotide probe prepared on the basis of the known nucleotide sequence of the purR gene. The nucleotide sequence of the purR gene from the *Bacillus subtilis* 168 Marburg strain has been reported [GenBank accession No. D26185 (the coding region corresponds to the nucleotide numbers 118041 to 118898), or NC_000964 (the coding region corresponds to the nucleotide numbers 54439 to 55296)]. The nucleotide sequence of the purR gene and the amino acid sequence encoded by the gene are shown in SEQ ID NOS: 5 and 6, respectively (Japanese Patent Laid-open No. 2004-242610).

Primers used to obtain the purR gene in PCR may be any primer which allows for amplification of a part or the full length of the purR gene, and specific examples include oligonucleotides having the nucleotide sequences shown in SEQ ID NO: 15 (GAAGTTGATGATCAAAA) and SEQ ID NO: 16 (ACATATTGTTGACGATAAT).

Examples of the marker gene include drug resistance genes such as the spectinomycin resistance and kanamycin resistance genes. The spectinomycin resistance gene from *Enterococcus faecalis* can be obtained by preparing the pDG1726 plasmid from *Escherichia coli* ECE101, which is commercially available from the *Bacillus* Genetic Stock Center (BGSC), and removing the resistance gene as a cassette from the plasmid. The erythromycin resistance gene from *Staphylococcus aureus* can be obtained by preparing the pDG646 plasmid from *Escherichia coli* ECE91, which is commercially available from the *Bacillus* Genetic Stock Center (BGSC), and removing the resistance gene as a cassette from the plasmid. The kanamycin resistance gene from *Streptococcus faecalis* can be obtained by preparing the pDG783 plasmid from *Escherichia coli* ECE94, which is commercially available from the *Bacillus* Genetic Stock Center (BGSC), and removing the resistance gene as a cassette from the plasmid. Furthermore, the chloramphenicol resistance gene from *Staphylococcus aureus* can be obtained by preparing the pC194 plasmid from *Bacillus subtilis* 1E17, which is commercially available from the *Bacillus* Genetic Stock Center (BGSC), and amplifying the plasmid by PCR using the plasmid as a template.

When a drug resistance gene is used as the marker gene, a strain with a disrupted purR gene can be obtained by inserting the drug resistance gene into the purR gene on a plasmid at an appropriate site, transforming the chosen microorganism with the plasmid, and selecting a drug-resistant transformant. Disruption of the purR gene on the chromosome can be confirmed by Southern blotting or PCR. Incorporation of the aforementioned spectinomycin resistance gene, erythromycin resistance gene, or kanamycin resistance gene into the chromosomal DNA can be confirmed by PCR using primers which can amplify these genes.

Expression of the purine operon is regulated by the terminator-antiterminator sequence located downstream of the promoter (henceforth referred to as the attenuator sequence) (Ebbole, D. J. and Zalkin, H., J. Biol. Chem., 1987, 262, 8274-8287; Ebbole D. J. and Zalkin H., J. Biol. Chem., 1988, 263, 10894-10902; Ebbole, D. J. and Zalkin, H., J. Bacteriol., 1989, 171, 2136-2141). Therefore, expression of the purine operon can be increased by deleting the attenuator sequence. The attenuator sequence can be deleted by the same method as for the disruption of purR.

In order to further increase transcription of the purine operon, any of the methods described above may be combined. For example, the purR gene may be disrupted, and further, the purine operon without the attenuator sequence may be amplified using a plasmid, or multiple copies of this modified purine operon may be introduced into the chromosome. The activities of enzymes involved in purine biosynthesis can also be enhanced by desensitizing enzymes which negatively regulate purine biosynthesis, for example, by desensitizing the enzymes which regulate feedback inhibition (WO99/03988). Furthermore, the ability to produce purine-derived substances can also be enhanced by attenuating the uptake of the purine-derived substances by the cells. For example, the uptake of purine nucleosides by the cells can be attenuated by blocking a reaction which facilitates this uptake. Examples of reactions involved in the uptake of the purine nucleosides by the cells include reactions which are catalyzed by nucleoside permeases.

Furthermore, when a purine nucleoside is produced, enzymes which act to decompose the purine nucleoside may be decreased, which will result in increased production of the purine nucleoside. An example of such an enzyme is purine nucleoside phosphorylase. Purine nucleotides which are synthesized from PRPP by enzymes involved in purine biosynthesis are dephosphorylated and thereby converted into a purine nucleoside. To efficiently produce a purine nucleoside, it is preferable to reduce the activity of purine nucleoside phosphorylases, which further degrade purine nucleosides into hypoxanthine or the like. That is, it is preferable to attenuate or eliminate the activity of the purine nucleoside phosphorylase that uses purine nucleosides, such as inosine, as a substrate.

Specifically, the purine nucleoside phosphorylase activity can be decreased by disrupting the deoD and pupG genes in *Bacillus* bacteria. The *Bacillus* bacterium may be modified by disrupting one or both of the deoD and pupG genes. The deoD and the pupG genes, for example, derived from or native to *Bacillus* bacteria (deoD: Genbank Accession No. NC_000964 (SEQ ID NO: 7), pupG: Genbank Accession No. NC_000964 (SEQ ID NO: 9)) can be used, and the gene-disrupted strain can be obtained in the same manner as that described for the aforementioned disruption of the purR gene.

The ability to produce a purine-derived substance may also enhanced by decreasing the activity of succinyl-AMP synthase. An example of the gene encoding succinyl-AMP synthase includes the purA gene. An example of the purA gene is the gene having the nucleotide sequence registered as GenBank Accession No. NC_000964 (coding region corresponds to the nucleotide numbers 4153460 to 4155749 of the complementary strand, SEQ ID NO: 11).

The ability to produce a purine-derived substance may also be enhanced by decreasing the activity of inosine monophosphate (IMP) dehydrogenase. An example of the gene encoding IMP dehydrogenase is the guaB gene. An example of the guaB gene is, for example, the gene having the nucleotide sequence registered as GenBank Accession No. NC_000964 (coding region corresponds to the nucleotide numbers 15913 to 17376, SEQ ID NO: 13).

Moreover, genes which encode proteins which act to enhance secretion of a purine-derived substance may be overexpressed in the method to increase the ability of a microorganism to produce purine-derived substances. An example of a bacterium in which such a gene has been overexpressed is a *Bacillus* bacterium in which the rhtA gene is overexpressed (Japanese Patent Laid-open No. 2003-219876).

The purR, deoD, pupG, purA, and guaB genes to be disrupted as described above, and the prs gene, which is to be overexpressed, may include conservative variants, for example, DNAs encoding proteins having the amino acid sequences of SEQ ID NOS: 6, 8, 10, 12, 14, 16, and 4, respectively, but which may contain substitutions, deletions, insertions, additions, or inversions of one or several amino acid residues and yet still maintain their native activity, that is, the activities of the purine repressor, purine nucleoside phosphorylase, succinyl-AMP synthase, IMP dehydrogenase or phosphoribosyl pyrophosphate synthetase, respectively. The number of amino acids to be changed may be, for example, 1 to 50, preferably 1 to 30, more preferably 1 to 10.

These changes in the amino acid sequences as described above are usually conservative changes so that the native activities are maintained. Examples of conservative amino acid substitutions include: substitution of Ser or Thr for Ala; substitution of Gln, H is or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Specific examples of conservative variants of the purR, deoD, pupG, purA, guaB and fbp genes and the prs gene described above include DNAs which are homologous, for example, 70% or more, preferably 80% or more, more preferably 90% or more, particularly preferably 95% or more, to DNAs having the nucleotide sequences of SEQ ID NOS: 5, 7, 9, 11, 13, 15 and 3, respectively. More specifically, the examples of the conservative variants include DNAs that are able to hybridize with DNAs having nucleotide sequences complementary to the nucleotide sequences of SEQ ID NOS: 5, 7, 9, 11, 13, 15 and 3 under stringent conditions. An example of the stringent conditions is washing at 60° C. and salt concentrations of 1×SSC, 0.1% SDS, preferably 0.1× SSC, 0.1% SDS, one or more times, preferably two or three times.

Homology of DNAs can be evaluated by a BLAST or FASTA search, the calculation method of Crustal W, and so forth.

BLAST (basic local alignment search tool) is a heuristic search algorithm used by the programs blastp, blastn, blastx, megablast, tblastn, and tblastx, and the results obtained by these programs are considered significant on the basis of the statistical method of Karlin, Samuel, and Stephen F. Altschul ("Methods for assessing the statistical significance of molecular sequence features by using general scoring schemes", Proc. Natl. Acad. Sci. USA, 1990, 87:2264-68; "Applications and statistics for multiple high-scoring segments in molecular sequences", Proc. Natl. Acad. Sci. USA, 1993, 90:5873-7). The FASTA search method was described by W. R. Pearson ("Rapid and Sensitive Sequence Comparison with FASTP and FASTA", Methods in Enzymology, 1990 183:63-98). The Clustal W method is described by Thompson J. D., Higgins D. G., and Gibson T. J. ("CLUSTAL W: Improving the sensitivity of progressive multiple sequence alignment through sequence weighting, position-specific gap penalties and weight matrix choice", Nucleic Acids Res., 1994, 22:4673-4680).

Moreover, DNA used to prepare the disrupted-type gene may also be conservative variants of the purR, deoD, pupG, purA or guaB genes.

The target gene may be incorporated into the chromosomal DNA of *Bacillus* bacterium in the same manner as that for the gene encoding fructose bisphosphatase described later.

(II) The Modification for Decreasing the Enzymatic Activity of Fructose Bisphosphatase The *Bacillus* bacterium can be obtained by modifying a strain having the ability to produce a purine-derived substance such as those described above so that the enzymatic activity of fructose bisphosphatase is decreased. The order of modification is not limited, and after modifying the bacterium so that the enzymatic activity of fructose bisphosphatase is decreased, the ability to produce purine nucleotides may be imparted to the bacterium.

Fructose bisphosphatase is an enzyme which catalyzes the reaction of generating fructose-6-phosphate from fructose-1,6-bisphosphate, which is one of the reactions of the glyconeogenesis pathway. The "glyconeogenesis pathway" means the pathway in which intracellular oxaloacetic acid is converted into phosphoenolpyruvic acid by decarboxylation catalyzed by phosphoenolpyruvate carboxykinase (EC: 4.1.1.49) and phosphorylation, phosphoenolpyruvic acid is converted into fructose-1,6-bisphosphate by the reverse reactions of the glycolytic enzymes, fructose-1,6-bisphosphate is further converted into fructose-6-phosphate by fructose bisphosphatase (EC: 3.1.3.11), and glucose is biosynthesized from fructose-6-phosphate by glucose-6-phosphate isomerase and glucose-6-phosphatase (EC: 3.1.3.9).

The enzymatic activity of fructose bisphosphatase can be measured by the following method. For example, it can be measured by converting the generated fructose-6-phosphate into NADPH by phosphoglucoisomerase and glucose-6-phosphate dehydrogenase, and measuring NADPH.

The modification which results in a decrease of the enzymatic activity of fructose bisphosphatase can be attained by, for example, as explained above for the disruption of the purR gene. That is, the enzymatic activity can be decreased by substituting a corresponding gene which does not function normally (e.g., a disrupted-type gene obtained by inserting a marker gene such as drug resistance gene into the fructose bisphosphatase gene) for the fructose bisphosphatase gene on the chromosome by homologous recombination. Furthermore, as described for the purR gene, mutations which result in reducing the intracellular enzymatic activity of fructose bisphosphatase may be introduced into the fructose bisphosphatase gene on the chromosome by conventional mutagenesis methods.

An example of fructose bisphosphatase of *Bacillus subtilis* is the protein having 671 amino acids as shown in SEQ ID NO: 2, and the gene encoding the protein, preferably the gene having the nucleotide sequence of SEQ ID NO: 1 (fbp gene, nucleotide numbers 4127053 to 4129065 of Genbank Accession No. NC_000964), can be used in the above described modification procedures. The fbp gene is located at about 323° on the *Bacillus subtilis* chromosome.

Examples of DNA encoding a protein substantially identical to fructose bisphosphatase include, specifically, a DNA encoding a protein having a homology of 50% or more, preferably 70% or more, more preferably 80% more, particularly preferably 90% or more, most preferably 95% or more, to the amino acid sequence shown in SEQ ID NO: 2, and having the enzymatic activity of fructose bisphosphatase.

The gene encoding fructose bisphosphatase may also be a conservative variant of the fbp gene, like the aforementioned genes. Specifically, examples include a DNA encoding a protein having the amino acid sequence of SEQ ID NO: 2, but which includes substitutions, deletions, insertions, additions, or inversions of one or several amino acid residues while maintaining the fructose bisphosphatase activity. Examples further include a DNA encoding a protein having a homology of 50% or more, preferably 70% or more, more preferably 80% more, particularly preferably 90% or more, most preferably 95% or more, to the amino acid sequence shown in SEQ ID NO: 2, and having the enzymatic activity of fructose bisphosphatase. More specifically, examples include a DNA which is able to hybridize with the DNA having the nucleotide sequence of SEQ ID NO: 1 under stringent conditions. The stringent conditions include washing at 60° C. and salt concentrations of 1×SSC, 0.1% SDS, preferably 60° C., 0.1× SSC, 0.1% SDS, one or more times, preferably two or three times.

The DNA encoding a protein substantially identical to fructose bisphosphatase as described above can be obtained, for example, by modifying the nucleotide sequence encoding such an enzyme so that an amino acid residue in a specific portion is substituted, deleted, inserted, added, or inverted by site-specific mutagenesis. Such a modified DNA as described above may also be obtained by a conventionally known mutagenesis treatment, such as in vitro treatment of DNA before the mutagenesis treatment with hydroxylamine, and treatment of a microorganism such as an *Escherichia* bacterium containing the DNA before the mutagenesis treatment with ultraviolet irradiation or a known mutagen, such as N-methyl-N'-nitro-N-nitrosoguanidine (NTG) or nitrous acid.

The target gene can be obtained by, for example, PCR (polymerase chain reaction, White, T. J. et al., Trends Genet., 1989, 5, 185-189) using a chromosomal DNA of a *Bacillus* bacterium as the template and oligonucleotide primers prepared based on the nucleotide sequence of the target gene. The chromosomal DNA can be prepared from a bacterium serving as a DNA donor by, for example, the method of Saito and Miura (H. Saito and K. Miura, Biochem. Biophys. Acta, 1963, 72, 619-629; Text for Bioengineering Experiments, Edited by the Society for Bioscience and Bioengineering, Japan, pp. 97-98, Baifukan, 1992), or the like. The primers for PCR can be prepared based on the known gene sequence from a *Bacillus* bacterium, or based on a conserved region among known genes from other bacteria.

Examples of the vector which can be used to incorporate the target gene into the chromosomal DNA of *Bacillus* bacterium include a vector having a temperature sensitive replication origin, such as pHV1248 (Prtit, M.-A., et. al., J. Bacteriol., 1990, 172, 6736-6740), vectors for *E. coli* such as pHSG398 (Takara Shuzo) and pBluescript SK− (Stratagene), and so forth.

In order to ligate the target gene to a vector carrying a marker which functions in *Bacillus* bacteria, the vector is digested with a restriction enzyme which generates sticky ends compatible with the objective gene. The ligation is usually performed with a ligase such as T4 DNA ligase.

To introduce the recombinant DNA vector prepared as described above into a *Bacillus* bacterium, any known transformation method can be employed. Examples include, for instance, preparing competent cells from cells which are at the growth phase followed by introducing the DNA thereinto, (Dubunau D. and Davidoff-Abelson, R., J. Mol. Biol., 1971, 56, 209-221), and making host cells into protoplasts or spheroplasts, which can easily take up recombinant DNA, followed by introducing the recombinant DNA into the DNA-acceptor cells (Chang, S, and Choen, S. N., Molec. Gen. Genet., 1979, 168, 111-115).

<2> Method for Producing a Purine-Derived Substance

The *Bacillus* bacterium prepared as described above efficiently produces a purine-derived substance. Therefore, by culturing the *Bacillus* bacterium as described above in an appropriate medium, a purine-derived substance, such as a purine nucleoside and a purine nucleotide can be produced and will accumulate in the bacterial cells or the medium.

The medium used in the culture can be any conventional medium which contains a carbon source, nitrogen source and mineral salts, as well as organic trace nutrients such as amino acids and vitamins, as required. Either a synthetic or natural medium may be used. Any carbon source and nitrogen source may be used so long as they can be utilized by a chosen strain.

As the carbon source, sugars such as glucose, fructose, sucrose, maltose, mannose, galactose, arabinose, xylose, trehalose, ribose, starch hydrolysates and molasses, and alcohols such as glycerol and mannitol can be used, and organic acids such as gluconic acid, acetic acid, citric acid, maleic acid, fumaric acid and succinic acid can also be used independently or in combination with other carbon sources.

As the nitrogen source, ammonia, ammonium salts such as ammonium sulfate, ammonium carbonate, ammonium chloride, ammonium phosphate and ammonium acetate, nitric acid salts, organic nitrogen such as soybean hydrolysate, and so forth can be used.

As the organic trace nutrients, amino acids, vitamins, fatty acids, nucleic acids, and substances containing these, such as peptone, casamino acid, yeast extract and soybean protein decomposition product, and so forth can be used. When an auxotrophic mutant strain that requires an amino acid or the like for growth is used, it is necessary to supplement the required nutrient.

As the mineral salts, phosphoric acid salts, magnesium salts, calcium salts, iron salts, manganese salts and so forth are used.

Although the culture conditions may vary depending on the type of *Bacillus* bacterium, *Bacillus subtilis*, for example, is cultured as an aeration culture, while the fermentation temperature is controlled to 20 to 50° C., and pH to 4 to 9. When pH falls during the culture, the medium is neutralized with an alkali such as ammonia gas. A purine nucleoside is produced into the medium after about 40 hours to 3 days of culture in such a manner as described above.

After completion of the culture, the purine-derived substance which has accumulated in the medium may be collected in a conventional manner. For example, it can be isolated by precipitation, ion exchange chromatography, and so forth.

Furthermore, if the chosen microorganism lacks a gene encoding a nucleosidase or nucleotidase, a corresponding nucleoside or nucleotide can be produced. Furthermore, if inosine auxotrophy is imparted, a precursor or relevant substances involved in the biosynthesis pathway thereof can be produced.

Furthermore, by reacting inosine or guanosine prepared by the described method with purine nucleoside phosphorylase or phosphoribosyltransferase, 5'-inosinic acid or 5'-guanylic acid can be obtained.

Moreover, it is also possible to phosphorylate the purine nucleoside produced using the microorganism as described herein by reacting phosphotransferase with the purine nucleoside to produce a purine nucleotide (nucleoside 5'-phosphoric acid ester) (Japanese Patent Laid-open No. 2000-295996). For example, the method for producing a purine nucleotide using an *Escherichia* bacterium transformed with the gene encoding inosine guanosine kinase of *Escherichia coli* (WO91/08286), and the method for producing a purine nucleotide using *Corynebacterium ammoniagenes* transformed with the gene encoding inosine guanosine kinase of *Exiguobacterium acetylicum* (WO96/30501) can be used.

Moreover, it is also possible to produce a purine nucleotide (nucleoside 5'-phosphoric acid ester) by reacting the purine nucleoside produced by the microorganism as described herein with a phosphate donor such as polyphosphoric acid, phenyl phosphate, and carbamyl phosphate, and a microorganism which is able to produce a nucleoside 5'-phosphoric acid ester or acid phosphatase (EC 3.1.3.2). Although the microorganism which is able to produce a nucleoside 5'-phosphoric acid ester is not particularly limited so long as it can convert a purine nucleoside into a purine nucleotide, examples include, for example, the microorganism disclosed in International Patent Publication WO96/37603.

Moreover, *Escherichia blattae* JCM 1650, *Serratia ficaria* ATCC 33105, *Klebsiella planticola* IFO 14939 (ATCC 33531), *Klebsiella pneumoniae* IFO 3318 (ATCC 8724), *Klebsiella terrigena* IFO 14941 (ATCC 33257), *Morganella*

*morganii* IFO 3168, *Enterobacter aerogenes* IFO 12010, *Enterobacter aerogenes* IFO 13534 (ATCC 13048), *Chromobacterium fluviatile* IAM 13652, *Chromobacterium violaceum* IFO 12614, *Cedecea lapagei* JCM 1684, *Cedecea davisiae* JCM 1685, *Cedecea neteri* JCM 5909, and so forth disclosed in Japanese Patent Laid-open No. 07-231793 can also be used.

The acid phosphatase, for example, disclosed in Japanese Patent Laid-open No. 2002-000289 can be used. The acid phosphatase with increased affinity to a nucleoside (Japanese Patent Laid-open No. 10-201481), a mutant acid phosphatase with decreased nucleotidase activity (WO96/37603), a mutant acid phosphatase with decreased phosphoric acid ester hydrolysis activity (Japanese Patent Laid-open No. 2001-245676), and so forth can more preferably be used.

It is also possible to obtain a purine nucleotide by chemically phosphorylating the purine nucleoside produced using the microorganism (Bulletin of the Chemical Society of Japan, 42, 3505). Moreover, the method of obtaining GMP by coupling the microorganism with the ability to produce XMP and XMP aminase activity using the ATP-regenerating system of the microorganism, and the method of obtaining IMP by coupling inosine kinase (Biosci. Biotech. Biochem., 51, 840 (1997); Japanese Patent Laid-open No. 63-230094) can also be used.

The inosine, guanosine, or purine nucleoside prepared by the above-described methods may be purified, a purine nucleoside fermentation broth, or a crude product containing a purine nucleoside.

EXAMPLES

Hereafter, the present invention will be more specifically explained with reference to the following non-limiting examples.

Example 1

Construction of a Bacterial Strain Deficient in the pupG and deoD Genes

A strain deficient in the purine nucleoside phosphorylase gene (deoD) was constructed from the recombinant strain KMBS310 as described below. The KMBS310 strain (Japanese Patent Application No. 2005-280186), which is derived from *Bacillus subtilis* (*B. subtilis* 168 Marburg strain, ATCC 6051), is deficient in the purine operon repressor gene (purR), succinyl-AMP synthase gene (purA), and purine nucleoside phosphorylase gene (pupG), and has an attenuated IMP dehydrogenase gene (guaB). In this strain, expression of the purine operon and the PRPP synthetase gene was enhanced by modifying the promoter region and the SD sequence, respectively.

Genomic DNA was prepared from the KMBS16 strain (purR::spc purA::erm deoD::kan, Japanese Patent Laid-open No. 2004-242610) by the method of Fouet and Sonenshein (J. Bacteriol., 1990, 172, 835-844), and was used to transform competent cells of the *B. subtilis* 168 Marburg strain prepared by the method of Dubnau and Davidoff-Abelson (J. Mol. Biol., 1971, 56, 209-221), and colonies grew on an LB agar plate containing 5 μg/ml of kanamycin. The colonies which did not became spectinomycin-resistant nor erythromycin-resistant were selected, and one strain among them was designated KMBS5 (deoD::kan).

Genomic DNA was prepared from KMBS5 by the method of Fouet and Sonenshein (J. Bacteriol., 1990, 172, 835-844), and was used to transform competent cells of the KMBS310 strain prepared by the method of Dubnau and Davidoff-Abelson (J. Mol. Biol., 1971, 56, 209-221), and colonies grew on an LB agar plate containing 5 μg/ml of kanamycin and 20 μg/ml of guanine. Several colonies were selected as described above, and one of the transformants was confirmed to have the deoD::kan substituted for the wild-type deoD gene, and all the mutations derived from KMBS310 were not replaced with wild-type sequences. This strain was designated KMBS321.

Example 2

Construction of a Bacterial Strain Deficient in the fbp Gene, Culture, and Evaluation Thereof (1) Preparation of the fbp Gene-Deficient Strain A strain deficient in the fructose bisphosphatase gene (fbp) was constructed from the aforementioned recombinant strain KMBS321 as described below. The KMBS321 strain, which is derived from *Bacillus subtilis* (*B. subtilis* 168 Marburg strain, ATCC 6051), is deficient in the purine operon repressor gene (purR), succinyl-AMP synthase gene (purA) and purine nucleoside phosphorylase gene (pupG), and has attenuated IMP dehydrogenase gene (guaB), and has a modified purine operon promoter region and SD sequence of the PRPP synthetase gene (prs).

(i) Amplification of fbp Upstream Region by PCR 28-mer and 50-mer PCR primers having the following nucleotide sequences were prepared based on the information from the public gene data bank (GenBank Accession Nos. NC_000964 and V01277).

TTCCCTTAGGGTTATTTTCGTTTCAAAA (SEQ ID NO: 17) cgtttgttgaactaatgggtgctTTTAT-GAGCATGTGCATGATAAGGTGA (SEQ ID NO: 18, the nucleotides indicated with small letters correspond to the promoter upstream region of the chloramphenicol resistance gene (cat) cloned in pC194)

PCR (98° C. for 10 second, 55° C. for 30 seconds, 72° C. for 1.5 minutes, 30 cycles, Gene Amp PCR System Model 9600, Perkin-Elmer) was performed using the chromosomal DNA of the *B. subtilis* 168 Marburg strain as the template and the aforementioned primers to obtain an amplification fragment containing the fbp gene 5' end region and about 1350 bp of the upstream region.

(ii) Amplification of fbp Downstream Region by PCR 50-mer and 27-mer PCR primers having the following nucleotide sequences were prepared based on the information from the public gene data bank (GenBank Accession Nos. NC_000964 and V01277).

acagctccagatccatatccttcttTTT-TAGAGAGTTTGCGGGAGTATCG (SEQ ID NO: 19, the nucleotides indicated with small letters correspond to a downstream region of structural gene of the chloramphenicol resistance gene (cat) cloned in pC194)

TAAAGGTTTTTCGGGATAAGATTGAAA (SEQ ID NO: 20)

PCR (98° C. for 10 second, 55° C. for 30 seconds, 72° C. for 1.5 minutes, 30 cycles, Gene Amp PCR System Model 9600, Perkin-Elmer) was performed using the chromosomal DNA of the *B. subtilis* 168 Marburg strain as the template and the aforementioned primers to obtain an amplification fragment containing the fbp gene 3' end region and about 1770 bp of the downstream region.

(iii) Amplification of Cat Gene by PCR 50-mer PCR primers having the following nucleotide sequences were prepared based on the information from the public gene data bank (GenBank Accession Nos. V01277 and NC_000964).

tcaccttatcatgcacatgctcat-aaaAGCACCCATTAGTTCAACAAACG (SEQ ID NO: 21, the nucleotides indicated with small letters correspond to the sequence of 5' end region of the fbp gene, and they were designed so as to be complementary to the 3' end region of SEQ ID NO: 18)

cgatactcccgcaaactctctaaaaAA-GAAGGATATGGATCTGGAGCTGT (SEQ ID NO: 22, the nucleotides indicated with small letters correspond to the sequence of 3' end region of the fbp gene, and they were designed so as to be complementary to the 3' end region of SEQ ID NO: 19)

PCR (98° C. for 10 second, 55° C. for 30 seconds, 72° C. for 1.5 minutes, 30 cycles, Gene Amp PCR System Model 9600, Perkin-Elmer) was performed using the plasmid pC194 carrying the chloramphenicol resistance gene (cat) as the template and the aforementioned primers to obtain an amplification fragment of about 980 bp containing the cat gene.

(iv) Amplification of Fragment Comprising fbp Region Inserted with the Cat Gene by Recombinant PCR The DNA fragments amplified in (i) to (iii) as described above were purified using MicroSpin Column S-400 (Amersham Pharmacia Biotech), and then a mixture of these primers in appropriate amounts was used as the template together with nucleotides having the sequences of SEQ ID NOS: 17 and 20 to perform PCR (98° C. for 10 second, 55° C. for 30 seconds, 72° C. for 4.5 minute, 30 cycles, Gene Amp PCR System Model 9600, Perkin-Elmer), and thereby obtain a fragment containing the fbp region with the cat gene inserted therein.

(v) Preparation of fbp-Disrupted Inosine-Producing Strain

The DNA fragment including the fbp region into which the cat gene (fbp::cat) obtained in (iv) had been inserted was subjected to agarose gel electrophoresis, and the target fragment was extracted from the gel. The DNA fragment purified as described above was used to transform competent cells of the *B. subtilis* KMBS321 strain prepared by the method of Dubnau and Davidoff-Abelson (J. Mol. Biol., 1971, 56, 209-221), and colonies grew on an LB agar plate containing 2.5 μg/ml of chloramphenicol and 20 μg/ml of guanine. Chromosomal DNAs were prepared from these colonies, strains in which fbp region on the chromosome was replaced with the fbp region of which internal sequence was replaced with the chloramphenicol resistance gene (fbp::cat) by double recombination were identified by the PCR method described in (iv), and one of these strains was designated TABS133.

(2) Production of a Purine Nucleoside by the Inosine-Producing Strain Deficient in the fbp Gene.

The fbp gene-deficient strain TABS133 and the control strain KMBS321 were each uniformly applied on an LB medium plate containing 20 mg/L of guanine, and cultured overnight at 34° C. The cells on ⅛ of the plate were inoculated into 20 ml of fermentation medium in a 500-ml volume Sakaguchi flask, then 50 g/L of calcium carbonate was added to the medium, and the cells were cultured at 34° C. with shaking. Seventy two hours after the start of the culture, the medium was sampled, and amounts of inosine and hypoxanthine present in the medium were measured by known methods. The amount of inosine which had accumulated with the fbp gene-deficient strain TABS133 was higher than that observed with the control KMBS321 strain.

Composition of Fermentation Medium:

| | |
|---|---|
| Glucose | 30 g/L |
| KH$_2$PO$_4$ | 1 g/L |
| NH$_4$Cl | 32 g/L |
| Mameno (T-N)* | 1.35 g/L |
| DL-Methionine | 0.4 g/L |

-continued

| | |
|---|---|
| L-Tryptophan | 0.02 g/L |
| Adenine | 0.1 g/L |
| Guanosine | 0.075 g/L |
| MgSO$_4$ | 0.4 g/L |
| FeSO$_4$ | 0.01 g/L |
| MnSO$_4$ | 0.01 g/L |
| Adekanol (antifoam) | 0.5 ml/L |
| (adjusted to pH 7.0 with KOH) | |
| Calcium Carbonate | 50 g/L |

*Soybean protein hydrolysate

TABLE 1

| B. subtilis strains | inosine (g/L) |
|---|---|
| KMBS321 | 5.3 |
| TABS133 | 5.8 |

Explanation of Sequence Listing

SEQ ID NO: 1: Nucleotide sequence of jbp gene

SEQ ID NO: 2: Amino acid sequence of fructose bisphosphatase

SEQ ID NO: 3: Nucleotide sequence of prs gene

SEQ ID NO: 4: Amino acid sequence of phosphoribosyl pyrophosphate synthetase

SEQ ID NO: 5: Nucleotide sequence of purR gene

SEQ ID NO: 6: Amino acid sequence of purine repressor

SEQ ID NO: 7: Nucleotide sequence of deoD gene

SEQ ID NO: 8: Amino acid sequence of deoD gene product (purine nucleoside phosphorylase)

SEQ ID NO: 9: Nucleotide sequence of pupG gene

SEQ ID NO: 10: Amino acid sequence of pupG gene product (purine nucleoside phosphorylase)

SEQ ID NO: 11: Nucleotide sequence of purA gene

SEQ ID NO: 12: Amino acid sequence of succinyl-AMP synthase

SEQ ID NO: 13: Nucleotide sequence of guaB gene

SEQ ID NO: 14: Amino acid sequence of IMP dehydrogenase

SEQ ID NO: 15: Primer for purR gene amplification

SEQ ID NO: 16: Primer for purR gene amplification

SEQ ID NO: 17: Primer for fbp gene upstream region amplification

SEQ ID NO: 18: Primer for fbp gene upstream region amplification

SEQ ID NO: 19: Primer for fbp gene downstream region amplification

SEQ ID NO: 20: Primer for fbp gene downstream region amplification

SEQ ID NO: 21: Primer for cat gene amplification

SEQ ID NO: 22: Primer for cat gene amplification

Industrial Applicability

By using the *Bacillus* bacterium of the present invention, production efficiency of a purine nucleoside and/or a purine nucleotide can be improved.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing a purine-derived substance, which comprises
   (A) culturing a bacterium belonging to the genus *Bacillus* which is able to produce a purine-derived substance in a medium, and
   (B) collecting the purine-derived substance from the bacterium or medium,
   wherein the bacterium has been modified to decrease the enzymatic activity of fructose bisphosphatase,
   wherein said fructose bisphosphatase is selected from the group consisting of:
      (i) a protein comprising the amino acid sequence of SEQ ID NO: 2,
      (ii) a protein comprising the amino acid sequence of SEQ ID NO: 2, but which includes substitutions, deletions, insertions, or additions, of one to 10 amino acid residues and has fructose bisphosphatase activity, and
      (iii) combinations thereof;
   wherein the fructose bisphosphatase activity is decreased by disrupting a gene encoding fructose bisphosphatase, or decreasing the expression of a gene encoding fructose bisphosphatase.

2. The method according to claim 1, wherein the purine-derived substance is a purine nucleoside or a purine nucleotide.

3. The method according to claim 2, wherein the purine-derived substance is a purine nucleoside selected from the group consisting of inosine, xanthosine, guanosine, and adenosine.

4. The method according to claim 2, wherein the purine-derived substance is a purine nucleotide selected from the group consisting of inosinic acid, xanthylic acid, guanylic acid, and adenylic acid, 5. A method for producing a purine nucleotide, which comprises
   (A) producing a purine nucleoside by the method according to claim 3,
   (B) reacting the purine nucleoside with a phosphate donor selected from the group consisting of polyphosphorie acid, phenyl phosphate, and carbamyl phosphate, and a microorganism which is able to produce a nucleoside-5'-phosphoric acid ester or acid phosphatase to produce a purine nucleotide, and
   (C) collecting the purine nucleotide.

6. The method according to claim 1, wherein the bacterium has been further modified to increase phosphoribosyl pyrophosphate synthetase activity.

7. The method according to claim 1, wherein the bacterium has been further modified to increase expression of the purine operon.

8. The method according to claim 7, wherein said expression is increased by disrupting a purR gene, wherein said purR encodes a repressor of the purine operon.

9. The method according to claim 1, wherein the bacterium has been further modified to decrease purine nucleoside phosphorylase activity.

10. The method according to claim 1, wherein the bacterium has been further modified to decrease IMP dehydrogenase activity.

11. The method according to claim 1, wherein the bacterium is *Bacillus subtilis*.

* * * * *